(12) United States Patent
Ratz et al.

(10) Patent No.: US 12,611,306 B2
(45) Date of Patent: Apr. 28, 2026

(54) DELIVERY SYSTEMS AND METHODS FOR PROSTHETIC HEART VALVE

(71) Applicant: inQB8 Medical Technologies, LLC, Winchester, MA (US)

(72) Inventors: J. Brent Ratz, Winchester, MA (US); Arshad Quadri, West Hartford, CT (US); Christopher Stivers, Somerville, MA (US); Devin Marr, Westford, MA (US)

(73) Assignee: inQB8 Medical Technologies, LLC, Burlington, MA (US)

( * ) Notice: Subject to any disclaimer, the term of this patent is extended or adjusted under 35 U.S.C. 154(b) by 0 days.

(21) Appl. No.: 18/024,011

(22) PCT Filed: Sep. 3, 2021

(86) PCT No.: PCT/US2021/049004
§ 371 (c)(1),
(2) Date: Feb. 28, 2023

(87) PCT Pub. No.: WO2022/051584
PCT Pub. Date: Mar. 10, 2022

(65) Prior Publication Data
US 2023/0263631 A1      Aug. 24, 2023

Related U.S. Application Data

(60) Provisional application No. 63/082,977, filed on Sep. 24, 2020, provisional application No. 63/074,185, filed on Sep. 3, 2020.

(51) Int. Cl.
*A61F 2/24* (2006.01)
*A61F 2/95* (2013.01)

(52) U.S. Cl.
CPC .......... *A61F 2/2439* (2013.01); *A61F 2/2418* (2013.01); *A61F 2/2436* (2013.01);
(Continued)

(58) Field of Classification Search
CPC ..................................................... A61F 2/2439
See application file for complete search history.

(56) References Cited

U.S. PATENT DOCUMENTS

| | | |
|---|---|---|
| 9,585,751 B2 | 3/2017 | Morriss et al. |
| 9,987,132 B1 | 6/2018 | Hariton et al. |
| (Continued) | | |

FOREIGN PATENT DOCUMENTS

| | | |
|---|---|---|
| EP | 2777617 A1 | 9/2014 |
| JP | 2016-512753 A | 5/2016 |
| (Continued) | | |

OTHER PUBLICATIONS

U.S. Appl. No. 18/175,644, filed Feb. 28, 2023, Ratz et al.
(Continued)

*Primary Examiner* — Rebecca S Preston
(74) *Attorney, Agent, or Firm* — Wolf, Greenfield & Sacks, P.C.

(57) ABSTRACT

Disclosed herein are delivery systems and methods for delivering a prosthetic heart valve to a native heart valve of a heart. An exemplary delivery system may include a shaft portion having at least one shaft, at least one steering wire, and at least one pull wire. The system may further include a handle portion coupled to a proximal end of the shaft portion and a capsule portion coupled to a distal end of the shaft portion. The capsule portion may be configured to house the prosthetic heart valve. At least one portion of the delivery system may be configured to be engaged with the prosthetic heart valve when the prosthetic heart valve is implanted in the native heart valve of the heart.

23 Claims, 26 Drawing Sheets

(52) U.S. Cl.
   CPC ................. *A61F 2002/9534* (2013.01); *A61F
         2210/0014* (2013.01); *A61F 2220/0075*
         (2013.01); *A61F 2220/0083* (2013.01); *A61F
         2230/001* (2013.01); *A61F 2250/0039*
         (2013.01); *A61F 2250/0069* (2013.01)

(56)                References Cited

U.S. PATENT DOCUMENTS

| | | | |
|---|---|---|---|
| 10,105,223 | B2 | 10/2018 | Savage et al. |
| 10,420,642 | B2 | 9/2019 | Gloss et al. |
| 10,617,519 | B2 | 4/2020 | Vidlund et al. |
| 10,687,939 | B2 | 6/2020 | Cooper et al. |
| 11,324,594 | B2 | 5/2022 | Ratz et al. |
| 11,602,433 | B2 | 3/2023 | Ratz et al. |
| 2002/0055775 | A1 | 5/2002 | Carpentier et al. |
| 2004/0127981 | A1 | 7/2004 | Rahdert et al. |
| 2005/0010287 | A1 | 1/2005 | Macoviak et al. |
| 2007/0088431 | A1* | 4/2007 | Bourang ............... A61F 2/2436 |
| | | | 623/2.11 |
| 2008/0071368 | A1 | 3/2008 | Tuval et al. |
| 2009/0005863 | A1 | 1/2009 | Goetz et al. |
| 2010/0049313 | A1* | 2/2010 | Alon ..................... A61F 2/2439 |
| | | | 623/2.11 |
| 2012/0035722 | A1 | 2/2012 | Tuval |
| 2012/0203336 | A1 | 8/2012 | Annest |
| 2013/0211508 | A1 | 8/2013 | Lane et al. |
| 2013/0325110 | A1 | 12/2013 | Khalil et al. |
| 2013/0325114 | A1 | 12/2013 | McLean et al. |
| 2014/0222136 | A1 | 8/2014 | Geist et al. |
| 2014/0277390 | A1 | 9/2014 | Ratz et al. |
| 2014/0277422 | A1 | 9/2014 | Ratz et al. |
| 2014/0277427 | A1 | 9/2014 | Ratz et al. |
| 2014/0316518 | A1* | 10/2014 | Kheradvar ............ A61F 2/2439 |
| | | | 623/2.11 |
| 2014/0379076 | A1 | 12/2014 | Vidlund et al. |
| 2015/0157477 | A1* | 6/2015 | Shahriari ................ A61F 2/962 |
| | | | 623/1.2 |
| 2015/0320556 | A1 | 11/2015 | Levi et al. |
| 2015/0342733 | A1 | 12/2015 | Alkhatib et al. |
| 2015/0351904 | A1 | 12/2015 | Cooper et al. |
| 2016/0008131 | A1 | 1/2016 | Christianson et al. |
| 2016/0095700 | A1 | 4/2016 | Righini |
| 2016/0310268 | A1* | 10/2016 | Oba ...................... A61F 2/2433 |
| 2017/0056166 | A1 | 3/2017 | Ratz et al. |
| 2017/0071733 | A1 | 3/2017 | Ghione et al. |
| 2017/0095328 | A1 | 4/2017 | Cooper et al. |
| 2017/0100236 | A1 | 4/2017 | Robertson et al. |
| 2017/0128199 | A1 | 5/2017 | Gurovich et al. |
| 2017/0216026 | A1 | 8/2017 | Quill et al. |
| 2017/0281341 | A1 | 10/2017 | Lim et al. |
| 2017/0319333 | A1 | 11/2017 | Tegels et al. |
| 2018/0021129 | A1 | 1/2018 | Peterson et al. |
| 2018/0028177 | A1* | 2/2018 | van Oepen ......... A61M 25/005 |
| 2018/0055629 | A1 | 3/2018 | Oba et al. |
| 2018/0116790 | A1* | 5/2018 | Ratz ...................... A61F 2/243 |
| 2018/0289485 | A1 | 10/2018 | Rajagopal et al. |
| 2018/0303612 | A1 | 10/2018 | Pasquino et al. |
| 2019/0008639 | A1 | 1/2019 | Landon et al. |
| 2019/0038405 | A1 | 2/2019 | Iamberger et al. |
| 2019/0069997 | A1 | 3/2019 | Ratz et al. |
| 2019/0083245 | A1 | 3/2019 | Hariton et al. |
| 2019/0083263 | A1 | 3/2019 | Hariton et al. |
| 2020/0038184 | A1 | 2/2020 | McLean |
| 2020/0155305 | A1 | 5/2020 | McLean |
| 2020/0205978 | A1 | 7/2020 | Padala et al. |
| 2020/0306044 | A1 | 10/2020 | Ratz et al. |
| 2021/0113332 | A1 | 4/2021 | Benichou et al. |
| 2021/0298902 | A1 | 9/2021 | Ratz et al. |
| 2021/0378822 | A1 | 12/2021 | Ratz et al. |
| 2022/0087816 | A1 | 3/2022 | Ratz et al. |
| 2024/0008984 | A1 | 1/2024 | Ratz et al. |

FOREIGN PATENT DOCUMENTS

| | | | |
|---|---|---|---|
| WO | WO 2018/213209 | A1 | 11/2018 |
| WO | WO 2019/010303 | A1 | 1/2019 |
| WO | WO 2019/010370 | A1 | 1/2019 |

OTHER PUBLICATIONS

PCT/US2020/024765, Jun. 15, 2020, International Search Report and Written Opinion.
PCT/US2020/024765, Sep. 2, 2021, International Preliminary Report on Patentability (Chapter II).
PCT/US2021/049004, Dec. 3, 2021, International Search Report and Written Opinion.
PCT/US2021/047906, Dec. 6, 2021, International Search Report and Written Opinion.
EP 20778511.4, Mar. 17, 2023, Extended European Search Report.
International Search Report and Written Opinion for International Application No. PCT/US2020/024765 mailed Jun. 15, 2020.
International Preliminary Report on Patentability (Chapter II) for International App. No. PCT/US2020/024765 dated Sep. 2, 2021.
International Search Report and Written Opinion for International Application No. PCT/US2021/049004 mailed Dec. 3, 2021.
International Search Report and Written Opinion for International Application No. PCT/US2021/047906 mailed Dec. 6, 2021.
Extended European Search Report for EP Application No. 20778511.4 dated Mar. 17, 2023.
Extended European Search Report for EP Application No. 21862806.3 dated Aug. 26, 2024.
Extended European Search Report for EP Application No. 21865164.4 dated Sep. 20, 2024.
EP 21862806.3, Aug. 26, 2024, Extended European Search Report.
EP 21865164.4, Sep. 20, 2024, Extended European Search Report.

* cited by examiner

1106

2302

2302

2302

2502 partial up

Fully
Down

Fully
up

Fully
Down partial up 2 sutures
from
fully up
RA arms 1 suture from
partial up 1 from partial
up 5 from
fully down
arms

.118

15.00°  R.100

Ø.420 liner    stent                                                      tube

6000

DELIVERY SYSTEMS AND METHODS FOR PROSTHETIC HEART VALVE

RELATED APPLICATIONS

This application is a national stage filing under 35 U.S.C. § 371 of international application number PCT/US2021/049004, filed Sep. 3, 2021, which claims priority under 35 U.S.C. § 119(e) to U.S. provisional application Ser. No. 63/074,185, filed Sep. 3, 2020 and to U.S. provisional application Ser. No. 63/082,977, filed Sep. 24, 2020, each of which is herein incorporated by reference in its entirety.

TECHNICAL FIELD

The present disclosure generally relates to implantable cardiac devices and, more particularly, to delivery systems for prosthetic heart valves.

BACKGROUND

Delivery systems have been used over time to deploy implants to various parts of the body. For example, delivery systems may be used to carry implants to the brain, the ear, the spine, various muscles, etc. Conventional systems are typically designed to carry implants while attempting to reduce possible trauma to the body during delivery. However, most systems are not successful in minimizing such harm. Additionally, an implant may be released by the delivery system in the body without the ability to adjust the position of or retrieve the implant after deployment.

SUMMARY

The disclosure provides delivery systems and methods for delivering a prosthesis, such as a prosthetic heart valve. Some embodiments include methods for delivering a prosthesis into the body, and/or securing a prosthesis to the native tissue, and/or removing a prosthesis from the body.

In one aspect, the disclosure features a delivery system for delivering a prosthetic heart valve to a native heart valve of a heart. The system may include a shaft portion having at least one shaft, at least one steering wire, and at least one pull wire. The system may further include a handle portion coupled to a proximal end of the shaft portion and a capsule portion coupled to a distal end of the shaft portion. The capsule portion may be configured to house the prosthetic heart valve. At least one portion of the delivery system may be configured to be engaged with the prosthetic heart valve when the prosthetic heart valve is implanted in the native heart valve of the heart.

Various embodiments of the delivery system may include one or more of the following features.

The capsule portion may include a tubular portion that comprises an expandable frame configured to expand beyond a perimeter of the tubular portion. The expandable frame comprises a plurality of frame members, and the one or more frame members are coupled to corresponding one or more portions of the prosthetic heart valve. One or more of the frame members comprise a fastener, and each fastener is configured to attach to the prosthetic heart valve. The delivery system may include a tube configured to maintain contact between each fastener and the prosthetic heart valve. The at least one pull wire may be attached to the tube.

The shaft portion comprises an inner shaft, and a distal portion of the inner shaft is disposed in a lumen of the tubular portion. The capsule portion may include a tapered head member coupled to the distal portion of the inner shaft. At least a portion of the tapered head member is disposed in the tubular portion. The shaft portion may include a plurality of nested shafts, and the plurality of nested shafts comprise the inner shaft. At least one shaft of the plurality of nested shafts may include at least one of an inner liner or an outer liner. The tubular portion may be configured to adjust a position of the prosthetic heart valve relative to the handle portion. The steering wire may be configured to flex the shaft portion to an angle up to approximately 125 degrees from a longitudinal axis of the handle portion. The steering wire may be configured to flex the shaft portion to an angle up to approximately 30 degrees from a longitudinal axis of the handle portion.

The at least one steering wire may include a first steering wire and a second steering wire. The first steering wire is configured to flex the shaft portion in a first plane from a longitudinal axis of the handle portion, and the second steering wire is configured to flex the shaft in a second plane from the longitudinal axis. A proximal end of the at least one pull wire may be disposed within the handle portion, and a distal end of the at least one pull wire is disposed within the capsule portion. The pull wire may be configured to control release of the prosthetic heart valve from the delivery system. The delivery system may include at least one tether for coupling the shaft portion to the prosthetic heart valve.

The at least one shaft may include an inner shaft disposed within a lumen of an outer shaft. The inner shaft may include at least one pin to which the at least one thread is coupled, the outer shaft may include at least one aperture through which the at least one thread is disposed, and a displacement of the inner shaft within the outer shaft may decouple the at least one thread from the at least one pin. The capsule portion may include a flexible tube configured to flex within at least one plane. The flexible tube may include a metal tube defining a first plurality of cutouts along a first side and a second plurality of cutouts along a second side, and the first side may be opposite the second side. The at least one portion of the delivery system may be configured to recapture the prosthetic heart valve. The at least one portion of the delivery system may be configured to access a native blood vessel to deliver the prosthetic heart valve to the heart.

In another aspect, the disclosure features a method for delivering a prosthetic heart valve to a native heart valve of a heart. The method may include advancing, by a delivery system comprising a capsule portion housing the prosthetic heart valve, the prosthetic heart valve through a native blood vessel and in proximity to the native heart valve; and implanting the prosthetic heart valve in the native heart valve such that a portion of the delivery system is engaged with the prosthetic heart valve when implanted.

Various embodiments of the method for delivering a prosthetic heart valve may include one or more of the following features.

The method may include expanding an expandable frame of the capsule portion, in which the expandable frame defines a space in which the prosthetic heart valve is disposed. The method may maintain engagement of the prosthetic heart valve, during the implanting step, via one or more hooks of the expandable frame. The method may release the prosthetic heart valve from the delivery system by retracting at least one pull wire of the delivery system, in which the pull wire is coupled to the one or more hooks of the expandable frame. The advancing step may include steering, via at least one steering wire of the delivery system, the capsule portion to the native heart valve. The method may include recapturing the prosthetic heart valve after implanting the prosthetic heart valve in the native heart valve.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Because aortic and mitral valve replacements have generally been the focus of device development, there exists a need for a solution for Tricuspid Regurgitation (TR), particularly because there is growing evidence showing that TR is associated with higher mortality rates and should not be left untreated even if the other heart valves have been addressed.

Examples of a prosthetic tricuspid valve and methods for implanting the same may be found in International Application No. PCT/US2020/024765, titled "PROSTHETIC HEART VALVE" and filed on Mar. 25, 2020 incorporated herein by reference in its entirety.

Figure 1:
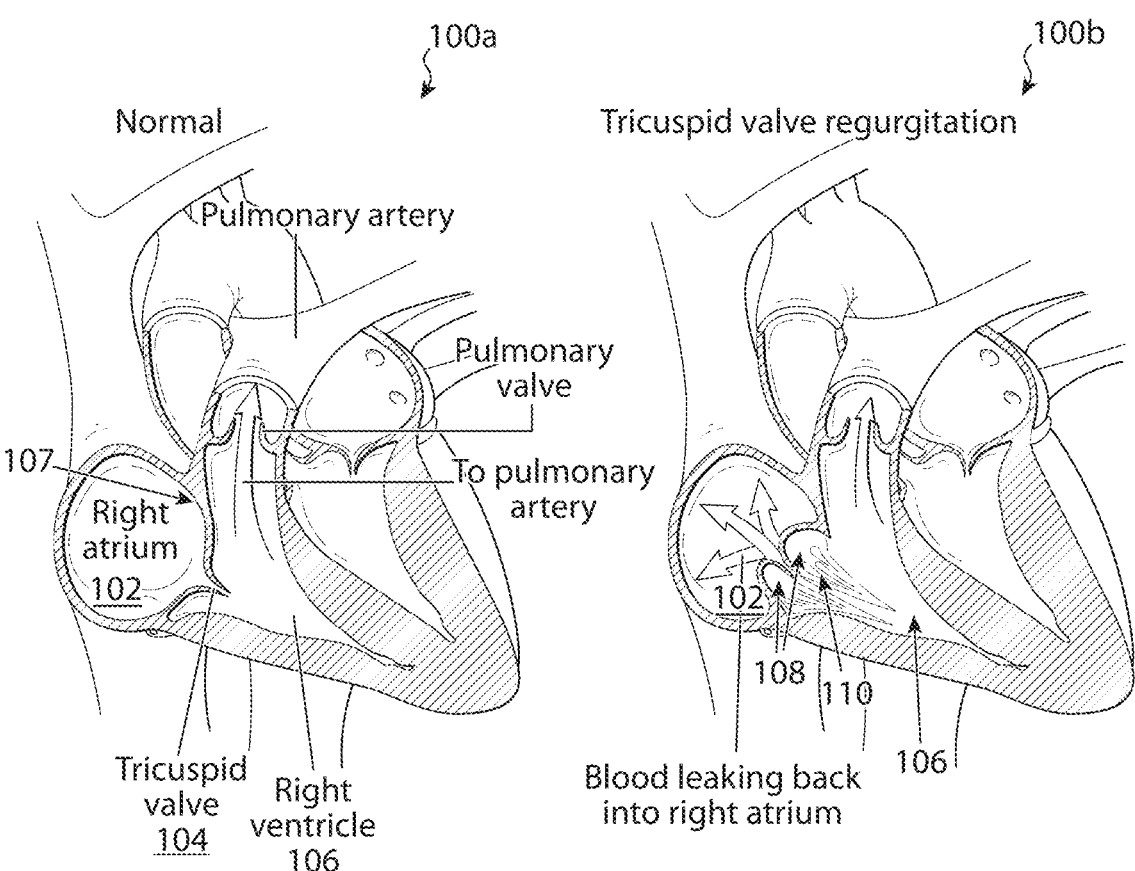
FIG. 1 is a cross-sectional view of the heart describing the anatomy of the right side of the heart during normal physiology and during the disease state of tricuspid regurgitation.

The tricuspid valve is in an atrio-ventricular position, located in the right side of the heart between the right atrium and the right ventricle, as shown in FIG. 1. FIG. 1 displays a side cross-sectional view of two versions 100*a*, 100*b* of a native heart. The version 100*a* depicts a normal anatomy of the native heart, in which blood flows from a right atrium 102 through a tricuspid valve 104 into a right ventricle 106, then through a pulmonary valve to the pulmonary artery. Separating the right atrium 102 from other parts of the heart (e.g., the left atrium) is the atrial septal wall 107. Version 100*b* depicts a native heart with tricuspid regurgitation, in which blood leaks from the right ventricle 106 through the tricuspid valve 104 and into the right atrium 102. Also depicted in FIG. 1 are two leaflets 108 of the native tricuspid valve 104 which, in version 100*b*, are shown having chordae 110 attached to the ventricular side of the leaflets and which serve to control the opening of the valve 104.

Figure 2:
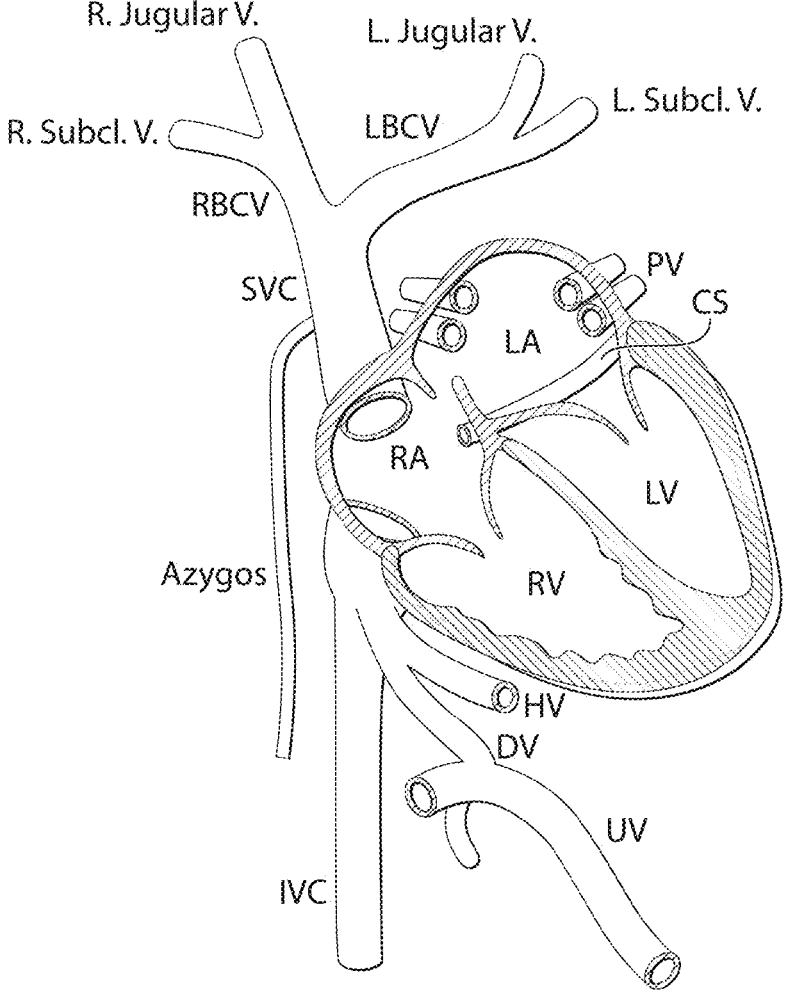
FIG. 2 is a cross-sectional view of the heart showing the venous pathways for accessing the right heart.

While the valve 104 may be accessed surgically, a less invasive approach has the potential to reduce perioperative and postoperative mortality associated with tricuspid valve surgery, and yet no transcatheter solution currently exists for complete replacement of the tricuspid valve. Transcatheter means of accessing the right heart are commonplace and most commonly use either the superior vena cava (SVC) via an incision in the jugular vein, or inferior vena cava (IVC) via incision in the femoral vein near the groin, as depicted in FIG. 2. While the innovations described herein are primarily intended for delivering a prosthetic heart valve to the native tricuspid valve, innovative aspects of such delivery systems may offer relevant improvements for delivery systems intended to reach other anatomical targets, such as any of the other three valves of the heart (i.e., pulmonary valve, aortic valve, and mitral valve). For example, the delivery system described herein could be used as described or with further modifications for treatment of defects of a septum of the native heart, or for accessing a left side of the native heart via trans-septal puncture, for example. In addition, the term "tricuspid valve" will be used herein in reference to a prosthetic valve that is preferentially intended for the tricuspid position but may also be used for other heart valves.

Delivery Systems for a Prosthetic Tricuspid Valve

Figure 3:
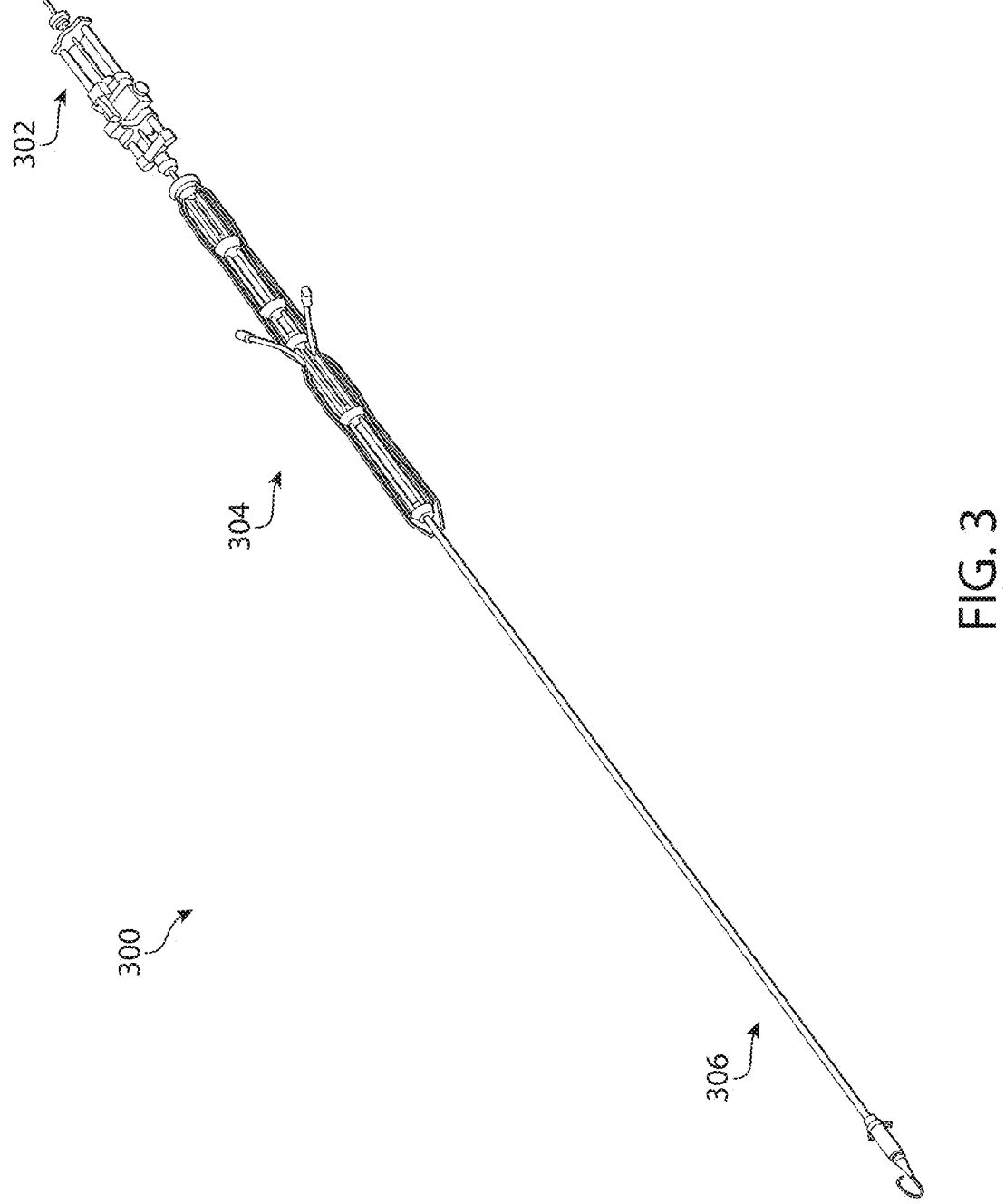
FIG. 3 is a perspective view of a delivery system, in accordance with an embodiment.

In accordance with aspects of the disclosure, a delivery system for a prosthetic tricuspid valve is provided herein. As shown in FIG. 3, the delivery system 300 includes a distal end and a proximal end, a handle portion 302 proximal to the proximal end, a shaft portion 304 distal to the handle portion, and a capsule portion 306 distal to the shaft portion. The delivery system 300 is configured to access a native blood vessel, for example the IVC or SVC, enter a right atrium of a native heart, and deliver a prosthetic tricuspid valve to a native tricuspid valve of the native heart. The delivery system 300 is further configured to flex the shaft portion of the delivery system in a first plane to an angle of at least 125 degrees. In some cases, the shaft portion 304 may be flexed to an angle of approximately 125 degrees (e.g., ±5 degrees, ±10 degrees, etc.). The delivery system 300 may be configured to flex the shaft portion 304 of the delivery system in a second plane to an angle of at least 30 degrees. In some cases, the shaft portion may be flexed in the second plane to an angle of approximately 30 degrees (e.g., ±1 degrees, ±3 degrees, etc.). The delivery system 300 may be configured to increase or decrease a depth of the prosthetic heart valve relative to the handle portion of the delivery system.

In some embodiments, the delivery system described herein is configured to deliver an implant (e.g., a prosthetic heart valve, a heart valve repair device, or the like) to a location internal of a subject. In some embodiments, the delivery systems described herein is configured to adjust the position of an implant, before deployment, during deployment, or after deployment. In some embodiments, the delivery system described herein is configured to retrieve the implant. The delivery systems described herein provide a number of advantages over previous implant delivery systems. For example, advantageously, the delivery systems described herein may be useful for delivering an implant, adjusting the position of the implant, and/or retrieving the implant after deployment, without damaging native tissue. In an exemplary set of embodiments, as described below in more detail, the delivery system is configured to deploy an implant such that the implant attaches to the native leaflets of a native heart valve. Other deployments and configurations are also possible and are described in more detail, below.

A "patient" or "subject" as used herein generally refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention described herein is directed toward use with humans. However, other subjects are also possible. In some embodiments, a subject may demonstrate health benefits, e.g., upon implantation of the valves described herein.

Although various examples are described herein in which prosthetic tricuspid valves are configured for replacement of the native tricuspid valve, it should be appreciated that appropriate modifications may be made for use of the prosthetic tricuspid valves disclosed herein to replace other native heart valves (e.g., other atrio-ventricular valves) and/or in any other non-heart valves.

In some exemplary embodiments, the delivery systems are configured to deploy a biodynamic prosthetic tricuspid valve. As referred to herein, the term "biodynamic" with regard to a prosthetic tricuspid valve, refers to a configuration of the prosthetic tricuspid valve that allows the prosthetic tricuspid valve to maintain axial stabilization within a native tricuspid valve of a heart, but to move within the native tricuspid valve responsive to alternating pressure differentials on either side of the native tricuspid valve during cardiac cycles of the heart, without directly attaching to a native annulus or native chords of the native tricuspid valve, thereby preserving the natural motion of the native annulus. Specifically, the prosthetic tricuspid valve is axially stabilized within the native tricuspid valve by grasping the native leaflets of the native tricuspid valve, rather than relying on annular force or direct annular or chordal attachment. As referred to herein, the term "axial stabilization" with regard to a prosthetic tricuspid valve located within a native tricuspid valve refers to a portion of the prosthetic tricuspid valve being interposed between any two diametrically opposed points on a native annulus of the native tricuspid valve.

In some embodiments, the prosthetic tricuspid valve includes one or more support structures. For example, as discussed in further detail below, the prosthetic tricuspid valve may include, in some cases, one, two, three, or more than three support structures. At least one of the one or more support structures includes, in some embodiments, a cylindrical portion having an atrial end and a ventricular end. In some embodiments, the cylindrical portion of the one or more support structures defines an elongate central passageway of the prosthetic tricuspid valve. In some embodiments, a central axis (also referred to as the "longitudinal axis") of the elongate central passageway extends within the elongate central passageway from the atrial end of the cylindrical portion to the ventricular end of the cylindrical portion. When the prosthetic tricuspid valve is in an implanted configuration in a native tricuspid valve of a heart, blood generally flows through the elongate central passageway of the prosthetic tricuspid valve from an atrium of the heart to a ventricle of the heart, along the central axis of the elongate central passageway. Furthermore, in some additional embodiments, a plurality of leaflet elements attaches to the one or more support structures and are disposed within the elongate central passageway for control of blood flow through the elongate central passageway.

In some embodiments, ventricular arms extending from a first end of the cylindrical portion of the one or more support structures extend into the ventricle of the heart to contact the ventricular surface of the native leaflets, while atrial arms extending from a second end opposite the first end of the cylindrical portion of the one or more support structures extend into the atrium to contact the atrial surface of the native leaflets. Advantageously, in some embodiments, various features of the prosthetic tricuspid valve described herein configure the valve for transcatheter implantation, re-positioning, and/or removal. For example, the prosthetic tricuspid valve described herein may be easily positioned and deployed in a wide range of patients with the ability to control the deployment, assess complete functionality, and/or maintain the ability to recapture and remove the implant prior to full release.

Figure 4:
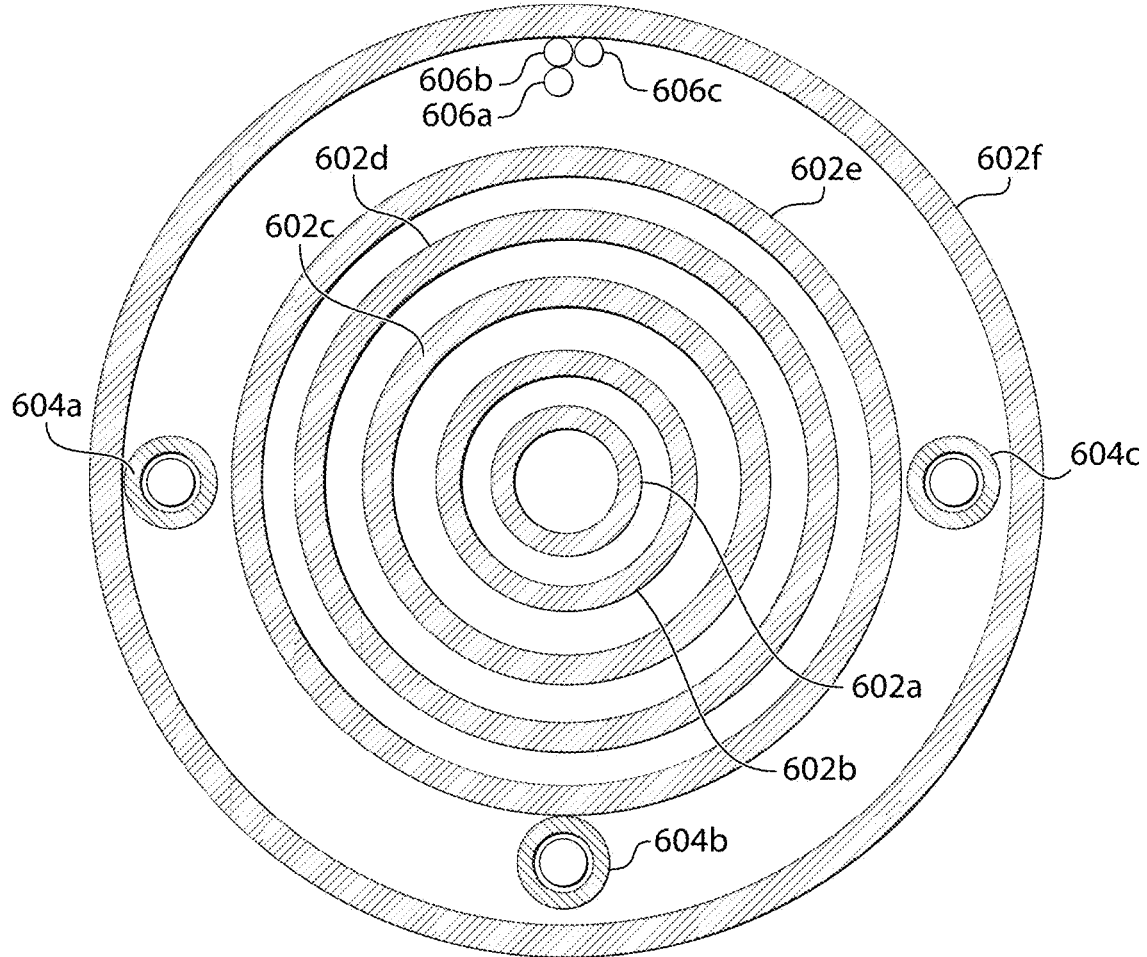
FIG. 4 is a cross-sectional view of a shaft portion of the delivery system of FIG. 3, in accordance with an embodiment.

In some embodiments, the delivery system 300 disclosed herein includes one or more shafts. FIG. 4 is a cross-sectional view of an embodiment wherein the shaft portion 304 of the delivery system 300 includes a first shaft 602a, a second shaft 602b, a third shaft 602c, a fourth shaft 602d, a fifth shaft 602e, and a sixth shaft 602f (collectively referred to as 602, of which only 602f is shown), a first steering wire 604a, a second steering wire 604b, a third steering wire 604c, a fourth steering wire 604d, and a fifth steering wire 604e (collectively referred to as 604), and three pull wires 606a, 606b, and 606c (collectively referred to as 606). In the embodiment of FIG. 4, the first shaft 602a is located within a lumen of the second shaft 602b, the second shaft 602b is located within a lumen of the third shaft 602c, the third shaft 602c is located within a lumen of the fourth shaft 602d, the fourth shaft 602d is located within a lumen of the fifth shaft 602e, and the fifth shaft 602e is located within a lumen of the sixth shaft 602f. In the embodiment of FIG. 4, the three pull wires 606 and the three steering wires 604 are located within a lumen of the sixth shaft 602f, but external to the fifth shaft 602e. Any of the shafts 602, pull wires 606, and/or steering wires 604 described herein may include an inner liner and/or an outer liner. Note that the wire used as a steering wire and pull wire may be any type of tether or linkages, e.g., line, cord, cable, rope, chain, etc. The inner and/or outer liners may be made of silicone, polyurethane (PU), polyethylene (PE), polyvinylchloride (PVC), polytetrafluoroethylene (PTFE), ethylene tetrafluoroethylene, (ETFE), fluorinated ethylene propylene (FEP), nylon, polyether block amide (PEBA), polyamide, other polymer materials, a hydrogel material such as a silicone hydrogel, or other flexible material.

In some embodiments, one or more of the pull wires 606 or steering wires 604 may include one or more lumens, for example one central lumen. In some embodiments, one or more of the pull wires 606 and/or steering wires 604 may include a solid wire, a ribbon, a flat wire, an elliptical wire, a wire with generally rectangular cross-section, etc. Any of the shafts may be made of a biocompatible material, preferably a metallic material such as Nitinol, stainless steel, titanium, or gold.

In the embodiment shown in FIG. 4, the first steering wire 604a is positioned radially approximately 180 degrees from the third steering wire 604c, the second steering wire 604b is positioned radially approximately 90 degrees from the first steering wire 604a and approximately 90 degrees from the second steering wire 604c, and the three pull wires 606 are positioned in close proximity approximately 90 degrees from both the first and second steering wires 604b, 604c. In other embodiments, the steering wires 604 and pull wires 606 may be positioned at different radial locations.

In some embodiments, any of the shafts 602, pull wires 606, and steering wires 604 may be configured to extend from the handle portion of the delivery system through the shaft portion 304 of the delivery system to the capsule portion 306 of the delivery system. Each of the shafts 602, pull wires 606, and steering wires 604 include a distal end and a proximal end, wherein the proximal ends of the shafts 602, pull wires 606, and/or steering wires 604 may be located within the handle portion 302 of the delivery system and the distal ends of the shafts 602, pull wires 606, and/or steering wires 604 may be located within the shaft portion 304 and/or the capsule portion 306 of the delivery system. In the embodiment of FIG. 4, the proximal ends of the three pull wires 606 are located within the handle portion 302 of the delivery system and the distal ends of the three pull wires 606 are located within the capsule portion 306 of the delivery system and are configured to control attachment of the delivery system to the prosthetic heart valve. In some embodiments, the delivery system may include fewer than three pull wires 606 or more than three pull wires 606. For example, the delivery system may include six or nine pull wires 606.

In the embodiment of FIG. 4, the distal ends of the three steering wires 604 are attached to the fifth shaft 602*e* and configured to enact a bend in the shaft portion 304 and/or capsule portion 306 of the delivery system by pulling one or more of the proximal ends of the steering wires 604. In the embodiment of FIG. 4, the first and third steering wires 604*a*, 604*c* are configured to enact a first bend in the six shafts 602 of the delivery system in a first direction of a first plane and a second bend in the six shafts 602 of the delivery system in a second direction of the first plane that is approximately opposite to the first direction of the first plane. The second steering wire 604*b* is configured to enact a third bend in the six shafts 602 of the delivery system in a first direction of a second plane that is approximately transverse to the first plane. Some embodiments may include fewer than three steering wires 604; for example, the delivery system may include only the first steering wire 604*a* of FIG. 4 and the third steering wire 604*c* of FIG. 4. Some embodiments may include more than three steering wires 604; for example, a fourth steering wire may be included to enact a fourth bend in the six shafts of the delivery system in a second direction of a second plane that is approximately opposite to the first direction of the second plane. In some embodiments, the steering wires 604 may be encircled by a protective tubes, which may be desirable to protect the steering wires 604 from damage, especially when the shaft portion of the delivery system is moved to a bent configuration. In some embodiments the protective tubes may be of a coil or helical shape.

In some embodiments, the delivery system disclosed herein is configured to deliver a prosthetic heart valve from a crimped configuration in which the prosthetic heart valve is enclosed within the capsule portion 306 of the delivery system, to an expanded configuration, in which the prosthetic heart valve is external to the capsule portion 306. The delivery system is further configured to position the prosthetic heart valve into a deployed configuration in the native tricuspid valve in which the prosthetic heart valve is engaged with one or more members of the capsule portion 306 of the delivery system. When in a deployed configuration, one or more aspects of the prosthetic heart valve are in direct communication with one or more aspects of the native tricuspid valve, such as one or more native leaflets of the native tricuspid valve, an annulus of the native tricuspid valve, one or more chordae of the native tricuspid valve, surrounding tissue of the native heart, etc. A benefit of the delivery system described herein is the ability to remain engaged with the prosthetic heart valve when in a deployed configuration, which allows assessment of the hemodynamic function of the prosthetic heart valve, prior to disengaging the prosthetic heart valve into an implanted configuration in the native heart.

In some embodiments, the delivery system is configured to position a prosthetic tricuspid valve from a deployed configuration to an expanded configuration, or from a deployed configuration to a crimped configuration, or from an expanded configuration to a crimped configuration. In such a way, an operator of the delivery system maintains the ability to completely remove the delivery system and prosthetic heart valve from the body after observing the hemodynamic assessment of the prosthetic heart valve, which may be in the best interest of the safety of the patient.

Figure 5:
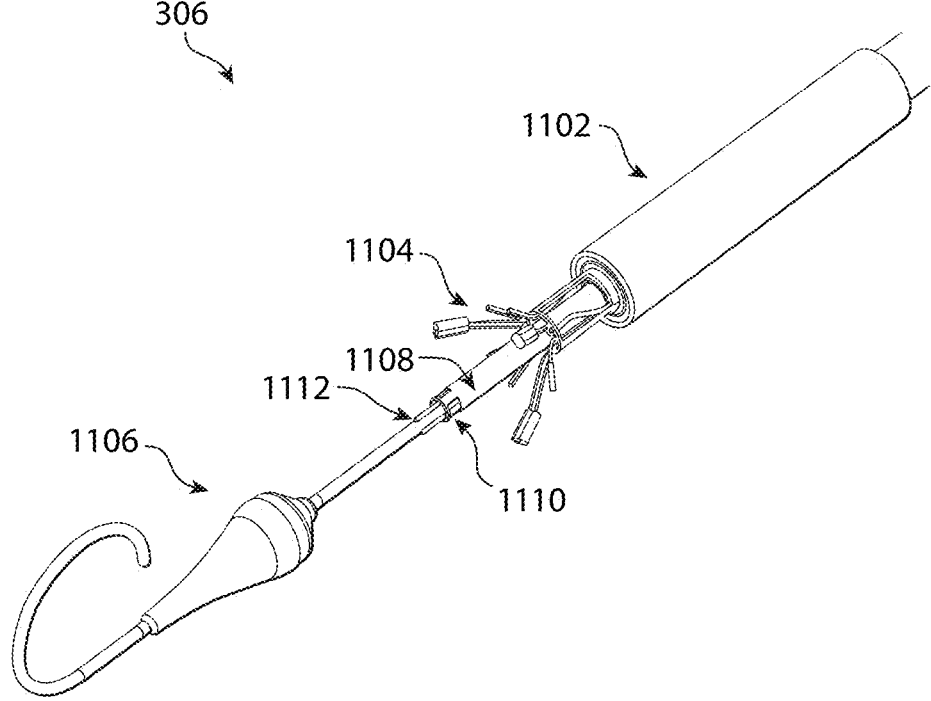
FIG. 5 is a perspective view of a distal end of the delivery system of FIG. 3, in accordance with an embodiment.

FIG. 5 depicts the capsule portion 306 of an embodiment in which the capsule portion 306 includes a tube 1102 configured to receive the prosthetic heart valve, an expandable frame 1104 configured to fit inside the tube 1102, the first shaft 602*a* of FIG. 4, the second shaft 602*b* of FIG. 4, and the third shaft 602*c* of FIG. 4, in which the first shaft 602*a* is configured to fit inside a lumen of the second shaft 602*b*, the second shaft 602*b* is configured to fit inside the third shaft 602*c*, and the third shaft 602*c* is configured to fit inside the expandable frame 1104. The capsule portion 306 further includes a tapered head member 1106 that in some embodiments is rigidly connected to a distal portion of the first shaft 602*a*. In some embodiments, the tube 1102 may include a single lumen with a distal end, a proximal end, and an intermediate portion disposed between the distal end and the proximal end, in which the first shaft 602*a*, second shaft 602*b*, third shaft 602*c*, and fourth shaft 602*d* are configured to extend through the lumen of the tube 1102 distally beyond the distal end of the tube 1102, the fifth shaft 602*e* is configured to extend within the lumen of the tube 1102 into the intermediate portion of the tube 1102, and the sixth shaft 602*f* is configured to extend within the lumen of the tube 1102 and rigidly attach to the intermediate portion of the tube 1102 such that the distal end of the sixth shaft 602*f* is proximal to the distal end of the fifth shaft 602*e*. In some embodiments, the distal end of the delivery system may be positioned at an angle between 70-90 degrees to the central axis (also referred to as a longitudinal axis) of an intermediate portion of the delivery system. In a preferred embodiment, the distal end is at an angle of approximately 75 degrees (e.g., ±5 degrees) to the central axis, which may be desirable for positioning the prosthetic heart valve in a native tricuspid valve when accessing the tricuspid valve via the SVC. In some embodiments, the distal end of the delivery system may be positioned at an angle between 90-130 degrees to the central axis of an intermediate portion of the delivery system. In a preferred embodiment, the distal end is at an angle of approximately 125 degrees (e.g., ±5 degrees) to the central axis, which may be desirable for positioning the prosthetic heart valve in a native tricuspid valve when accessing the tricuspid valve via the IVC.

In some embodiments, capsule portion 306 further comprises inner tube 1108 comprising one or more (e.g., two or more, three or more, four or more) apertures 1110. In some embodiments, capsule portion 306 further comprises pins 1112, moveable independently of, and disposed within inner tube 1108. Apertures and pins are described in more detail, below.

In some embodiments, the distal portion of the first shaft 602*a* has at least one curve, which may be advantageous to prevent the capsule portion 306 of the delivery system from damaging or becoming entangled in tissue of the native heart or tissue of the native blood vessels. In some embodiments, the first shaft 602*a* may be configured to deliver a contrast agent to the native heart, which may be desirable to facilitate visualization of the hemodynamics of the heart before or after implantation of the prosthetic heart valve with the use of fluoroscopic imaging.

Figure 6:
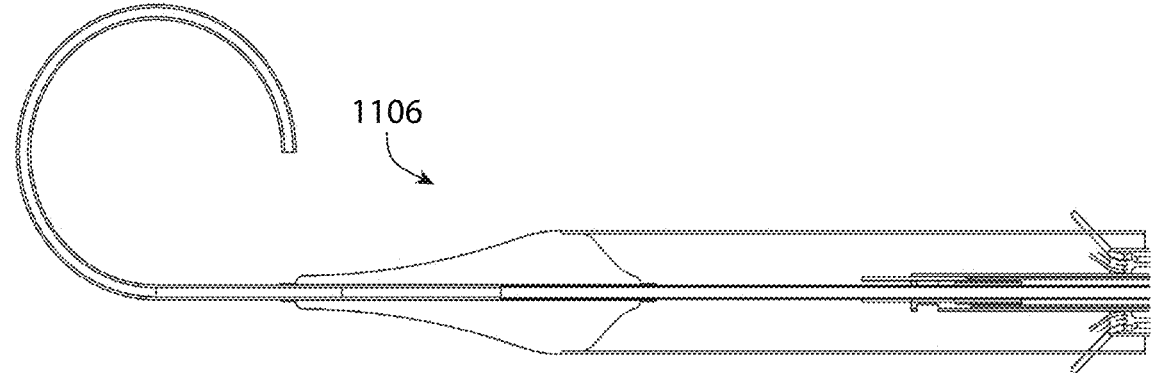
FIG. 6 is a cross-sectional view of the capsule portion of the delivery system of FIG. 3, in accordance with an embodiment.

The tapered head member 1106 of FIG. 5 has a distal portion, an intermediate portion, and a proximal portion, in which the distal portion has a diameter that is smaller than a diameter of the intermediate portion, and the proximal portion has a diameter that is smaller than a diameter of the intermediate portion. In some embodiments, the proximal portion is configured to nest securely within the tube of the capsule portion, as shown in FIG. 6. As shown in FIG. 6, the maximum diameter of the intermediate portion is greater than the maximum diameter of the proximal portion of the tapered head member, and the diameter of the proximal portion is sized to fit snugly within a distal portion of the tube, while the maximum diameter of the intermediate portion is sized to approximately match the outer diameter of the distal portion of the tube. In this way, the tapered head member may be securely nested within the tube to prevent unintentional disengagement with the tube, which could otherwise expose a distal edge of the tube and potentially cause damage to the native tissue during use.

Referring again to FIG. 5, the tapered head member 1106 may be made from any kind of flexible material, such as PTFE, polyester, silicone, PU, PE, PVC, PTFE, ETFE, FEP, PEBA, polyamide, or a hydrogel material. In a preferred embodiment, the tapered head member 1106 is made from a urethane or polyurethane (PU). In some embodiments, the tapered head member 1106 may further include a coating, covering, liner, or film configured to increase the lubricity of the tapered head member 1106, which may facilitate insertion of the delivery system through a blood vessel of the body. In some embodiments, the tapered head member 1106 may also include one or more radiopaque components, for example, at a distal end and/or at a proximal end of the tapered head member 1106, which may be desirable to easily identify the full length of the tapered head member 1106 with the use of fluoroscopic imaging.

In some embodiments, the one or more pins located at the distal end of the second shaft are configured to engage with one or more arms of the prosthetic heart valve. In some embodiments, the delivery system (e.g., via the one or more pins) is configured to raise and/or lower the arms of the prosthetic heart valve (e.g., such that it may be positioned). In an exemplary set of embodiments, the delivery system is configured to engage with one or more arms of the prosthetic heart valve (e.g., an atrial set of arms and/or a ventricular set of arms of the prosthetic heart valve) such that the one or more arms may be raised or lowered. Advantageously, the delivery system described herein may be configured to raise and/or lower the arms of the prosthetic heart valve such that the prosthetic heart valve may be (re)positioned into a final anchored state (e.g., attached to the native leaflets of the native heart valve)

Figure 7A:
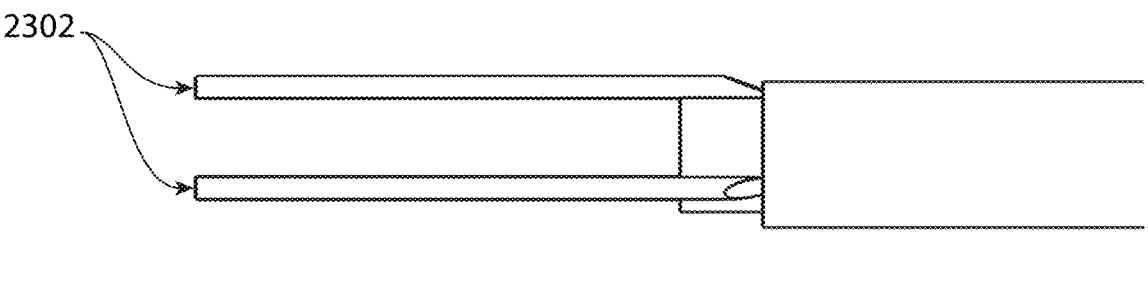
FIG. 7A is a side view of a distal end of a third shaft of the delivery system of FIG. 3, in accordance with an embodiment.
Figure 7B:
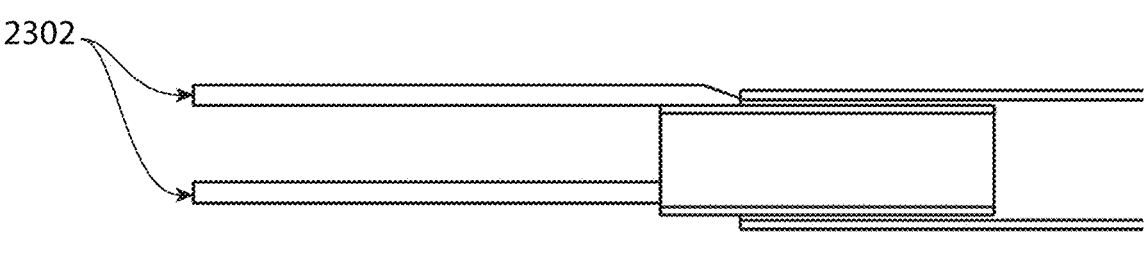
FIG. 7B is a side cross-sectional view of a distal end of a third shaft of the delivery system of FIG. 3, in accordance with an embodiment.

In some embodiments, such as the ones shown in FIGS. 7A-7B, the second shaft 602b of the capsule portion 306 of the delivery system further includes one or more generally cylindrically-shaped pins 2302, each pin having a proximal end with a proximal face and a distal end with a distal face. The one or more pins can be located at the distal end of the second shaft. In some embodiments, a distal end of each of the one or more pins 2302 can extend further distally than the distal end of the second shaft. In some embodiments, the one or more pins 2302 may include three pins and may be equally spaced around a perimeter of the second shaft and aligned in a parallel direction with the third shaft. In some embodiments, the distal faces of the three pins 2302 may be approximately parallel. In some embodiments the one or more pins may be rigidly connected to the second shaft, for example, by welding, soldering, adhesive bonding, or through other mechanical connection. In some embodiments, the one or more pins and the second shaft may be formed from a single component, for example by laser cutting, machining, electrical discharge machining (EDM), casting, extrusion, etc.

Figure 7C:
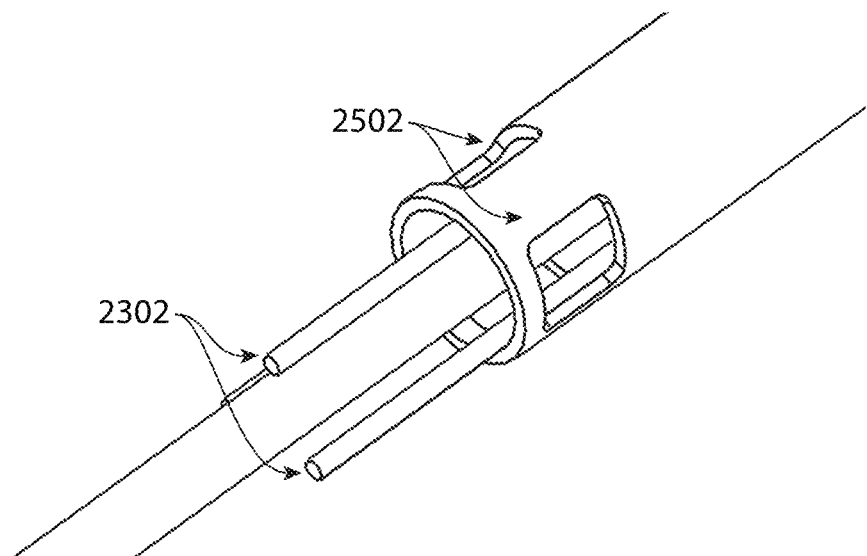
FIG. 7C is a perspective view of a distal end of a third shaft of the delivery system of FIG. X3, in accordance with an embodiment.
Figure 7D:
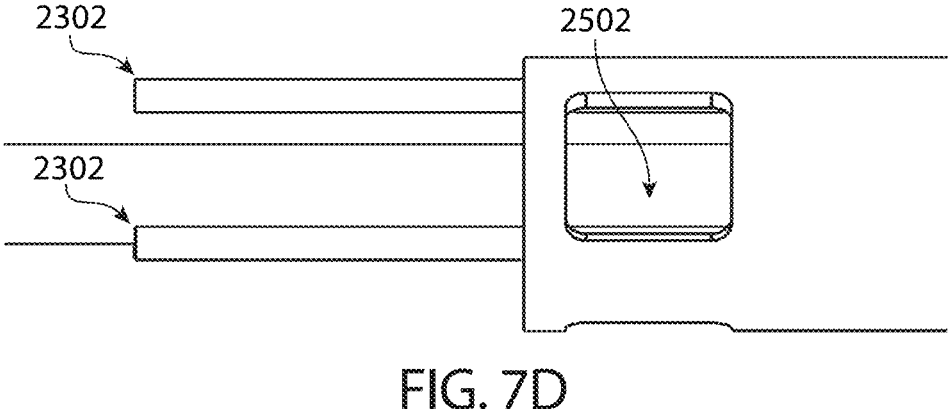
FIG. 7D is a side view of a distal end of a third shaft of the delivery system of FIG. 3, in accordance with an embodiment.
Figure 7E:
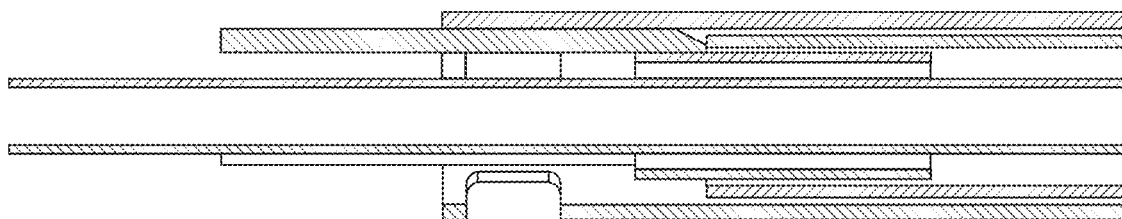
FIG. 7E is a cross-sectional side view of a distal end of a third shaft of the delivery system of FIG. 3, in accordance with an embodiment.

In some embodiments, such as the embodiment depicted in FIGS. 7C-7E, the third shaft 602c includes a proximal end and a distal end. In some embodiments, the distal end of the third shaft includes one or more apertures 2502. In some embodiments, the one or more apertures may include three apertures and may be equally spaced around a circumference of the third shaft 602c. In some embodiments, the one or more apertures 2502 are located near the distal end of the third shaft 602c. In some embodiments, the shape of the third shaft 602c defines an approximately rectangular shape of the one or more apertures 2502, although in other embodiments, the aperture 2502 may have a circular, elliptical, or other geometric shape.

In some embodiments, such as the one depicted in FIGS. 7C-7E, the distal ends of the one or more pins 2302 of the second shaft 602b are located more distally than the distal end of the third shaft 602c. In some embodiments, the distal end of the third shaft 602c is located more distally than the distal end of the second shaft.

Figures 8A, 8B:
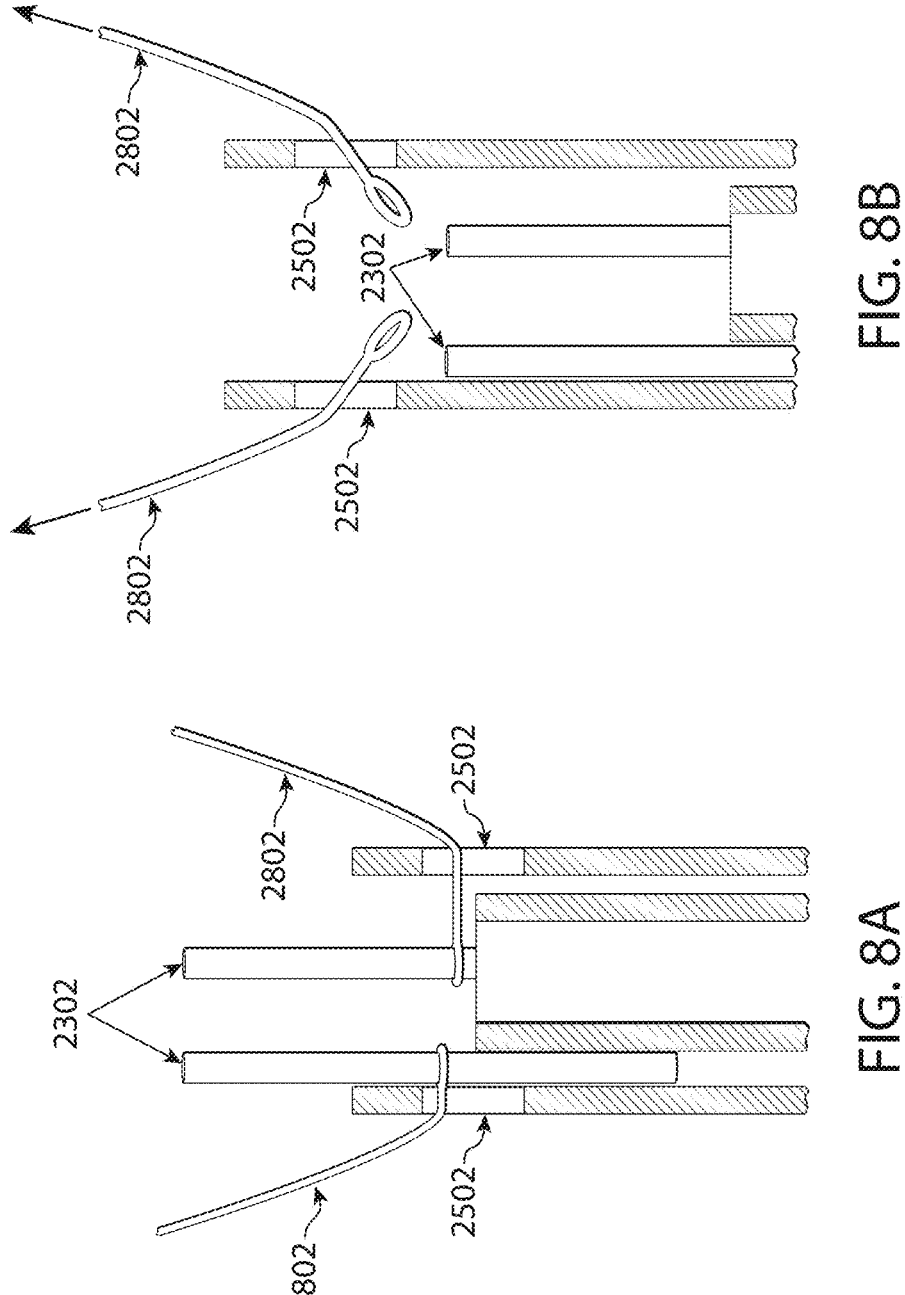
FIGS. 8A-8B illustrate two cross-sectional views of the distal ends of the second and third shafts of the delivery system of FIG. 3, in accordance with an embodiment.
Figure 8C:
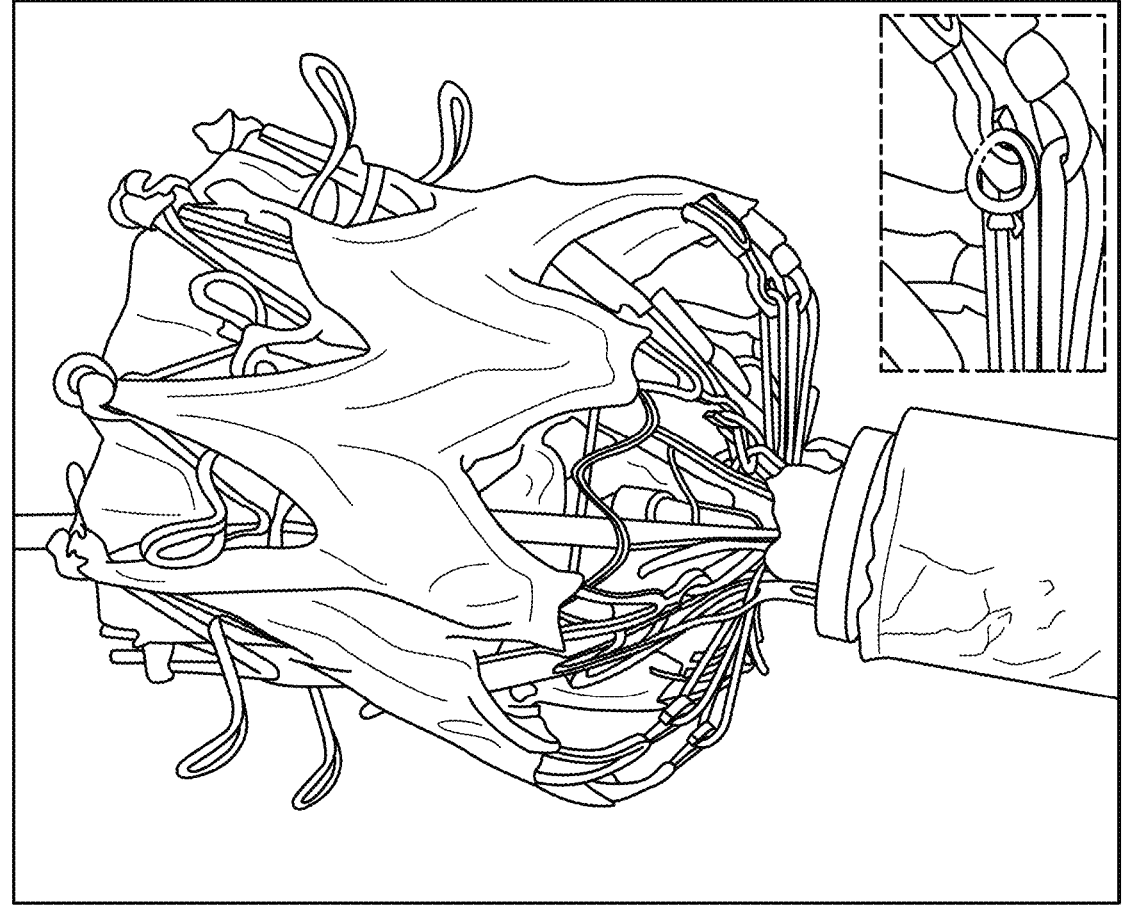
FIG. 8C is a perspective view of a prosthetic heart valve attached to a delivery system, in accordance with an embodiment.

In the embodiment of FIGS. 8A and 8B, the capsule portion 306 of the delivery system may further include one or more thread-like elements 2802 having a first end and a second end, in which the first end may be configured to attach to the one or more pins 2302 of the second shaft, and the second end may be configured to attach to a portion of the prosthetic heart valve. In the embodiment of FIGS. 8A and 8B, one or more thread-like elements 2802 may be fed through the one or more apertures 2502 of the third shaft 602c. The second shaft 602b may be configured to move in an axial direction relative to the third shaft 602c so that when the distal end of the second shaft 602b is moved proximally relative to the distal end of the third shaft 602c, the distal end of the one or more pins 2302 may be moved more proximally than the location of the one or more apertures 2502 of the second shaft 602b. In this way, the relative movement of the second and third shafts 602b, 602c may bring about a release of the one or more thread-like elements 2802 from the one or more pins 2302 of the second shaft 602b. In some embodiments, the first end and/or the second end of the thread-like element 2802 may be configured to form a loop, which may be advantageous to facilitate attachment to the one or more pins 2302 or to the prosthetic heart valve. In some embodiments, the second shaft 602b and/or the third shaft 602c may be configured to prevent axial movement beyond a certain distance, for example, to prevent the second shaft 602b from moving too far distally with respect to the third shaft 602c, which could otherwise risk damage to the prosthetic heart valve and/or to one or more thread-like elements 2802.

Figure 9:
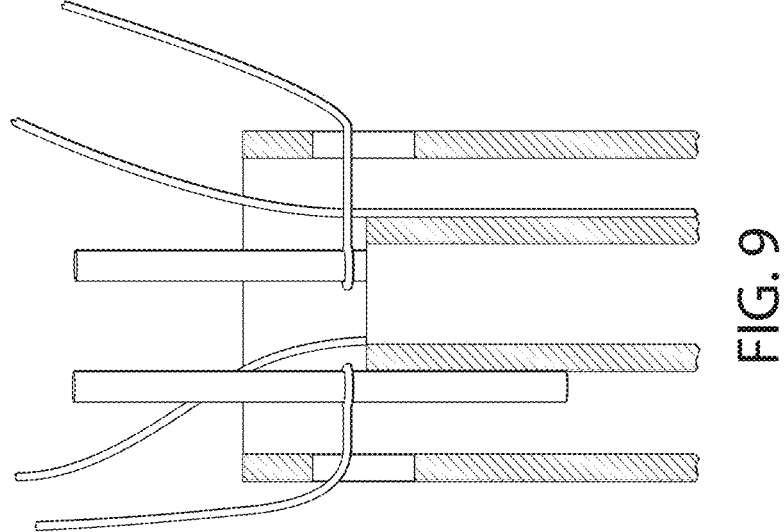
FIG. 9 is a cross-sectional view of the distal ends of the second and third shafts of the delivery system of FIG. 3, in accordance with an embodiment.

The embodiment of FIG. 9 includes one or more thread-like elements 2802 which may include a first end, a second end, and an intermediate portion disposed between the first end and the second end, in which the first end is attached to a portion of the second shaft and the second end is attached to the one or more pins of the second shaft. The intermediate portion of the one or more thread-like elements is configured to exit the distal end of the third shaft, attach to a portion of the prosthetic heart valve, and pass through the one or more apertures of the third shaft. In the embodiment of FIG. 9, the first end is securely attached to the second shaft, while the second end is attached to the one or more pins of the second shaft in such a way that the second end may become unattached from the one or more pins when the distal end of the one or more pins is brought to be more proximal than the one or more apertures of the third shaft, such as the release of the one or more thread-like elements displayed in FIGS. 8A and 8B.

Figure 10:
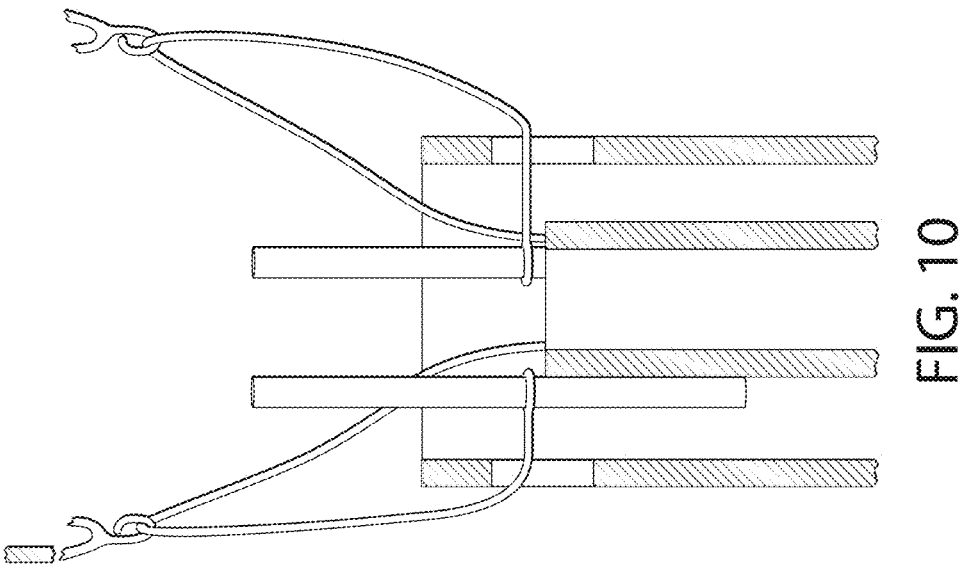
FIG. 10 is a cross-sectional view of the distal ends of the second and third shafts of the delivery system of FIG. 3, in accordance with an embodiment.

In the embodiment of FIG. 10, a first end and a second end of the one or more thread-like elements are rigidly attached to a portion of the second shaft. The intermediate portion of the thread-like element is configured to exit the distal end of the third shaft, attach to a portion of the prosthetic heart valve, and pass through the one or more apertures of the third shaft. The intermediate portion of the thread-like element is further configured to attach to the one or more pins of the first shaft in such a way that movement of the distal end of the first shaft proximally relative to the distal end of the second shaft may bring about the release of the thread-like element from the one or more pins of the first shaft.

FIG. 8A depicts an embodiment of the delivery system in which the one or more thread-like elements 2802 include nine thread-like elements have a first set of ends that is attached to the prosthetic heart valve and a second set of ends that is attached to the pins of the second shaft. In some such embodiments, the third shaft includes three apertures, in which three thread-like elements are attached to each pin of the second shaft and three intermediate portions of the thread-like elements each pass through one of the apertures of the third shaft. The second shaft and third shaft may be configured to move axially relative to other elements of the delivery system to transition the prosthetic heart valve from an expanded configuration to a deployed configuration, and vice versa. The second and third shaft may be further configured to move axially relative to one another to transition the prosthetic heart valve from a deployed configuration to an implanted configuration.

Figure 8D:
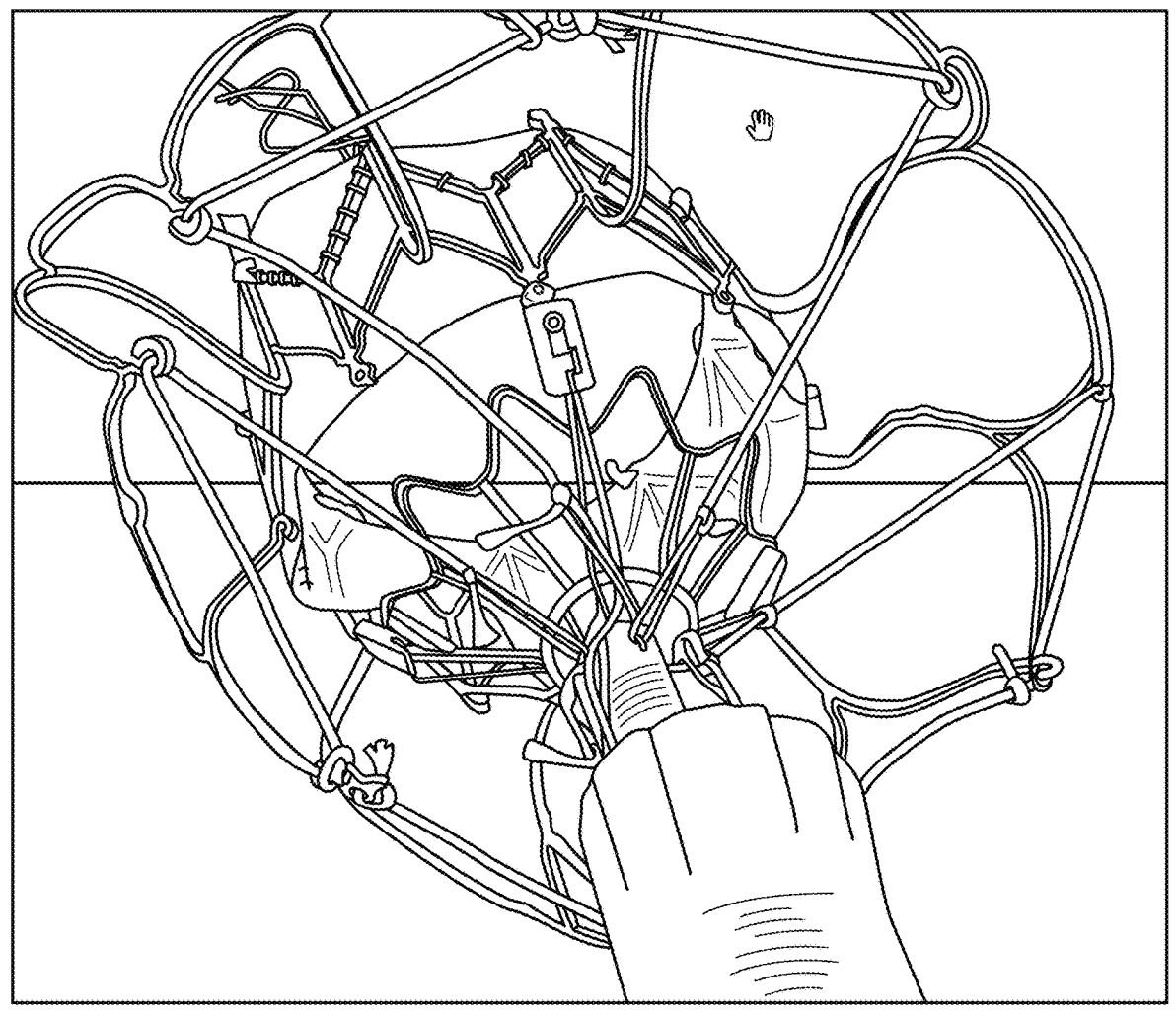
FIG. 8D is a perspective view of a prosthetic heart valve attached to a delivery system, in accordance with an embodiment.

FIG. 8D depicts an embodiment of the delivery system in which the one or more thread-like elements include six thread-like elements having a first set of ends that is attached to the prosthetic heart valve and a second set of ends that is attached to the pins of the second shaft. In some such embodiments, the third shaft includes three apertures, in which two thread-like elements are attached to each pin of the second shaft and two intermediate portions of the thread-like elements each pass through one of the apertures of the third shaft. The method of routing the thread-like elements through portions of the prosthetic heart valve as shown in 8D may be advantageous to reduce the number of thread-like elements required, or to reduce the time required to attach the thread-like elements to the delivery system and/or to the prosthetic heart valve. Other embodiments may include greater or fewer numbers of thread-like elements and apertures, with different configurations of thread-like elements exiting through the apertures.

Figure 11B:
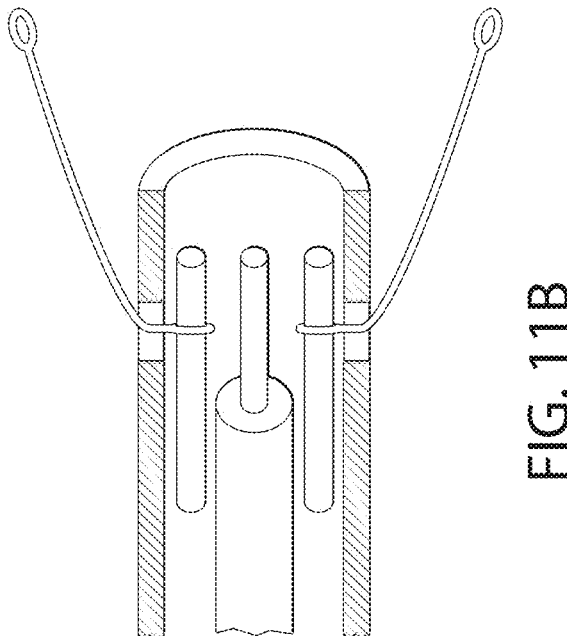
FIGS. 11A-11B illustrate two thread-like elements configured to attach a prosthetic heart valve to a delivery system, in accordance with an embodiment.
Figure 11A:
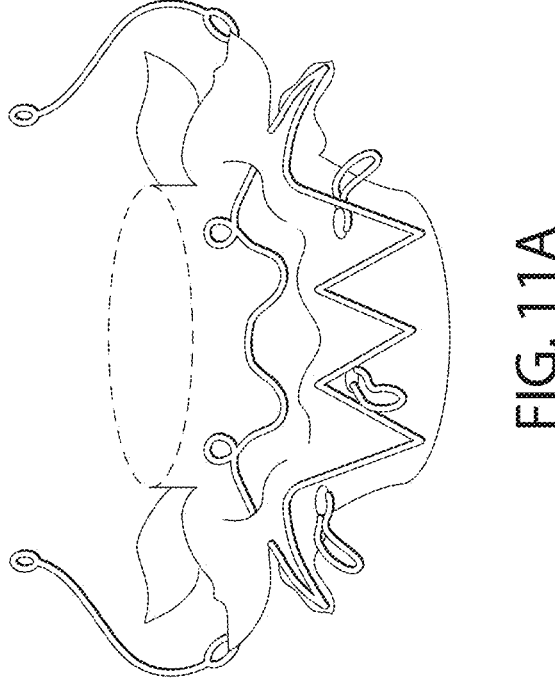

In some embodiments, such as the ones shown in FIGS. 11A and 11B, the prosthetic heart valve may include one or more thread-like elements that each have a first end with a first loop and a second end with a second loop. In the embodiments of FIGS. 11A and 11B, the first loop may be attached to the prosthetic heart valve and the second loop may be attached to the one or more pins of the second shaft. The second and third shafts may be operated as previously described to disengage the one or more second loops from the one or more pins of the second shaft, thereby releasing and implanting the prosthetic heart valve and the one or more thread-like elements.

Figure 12:
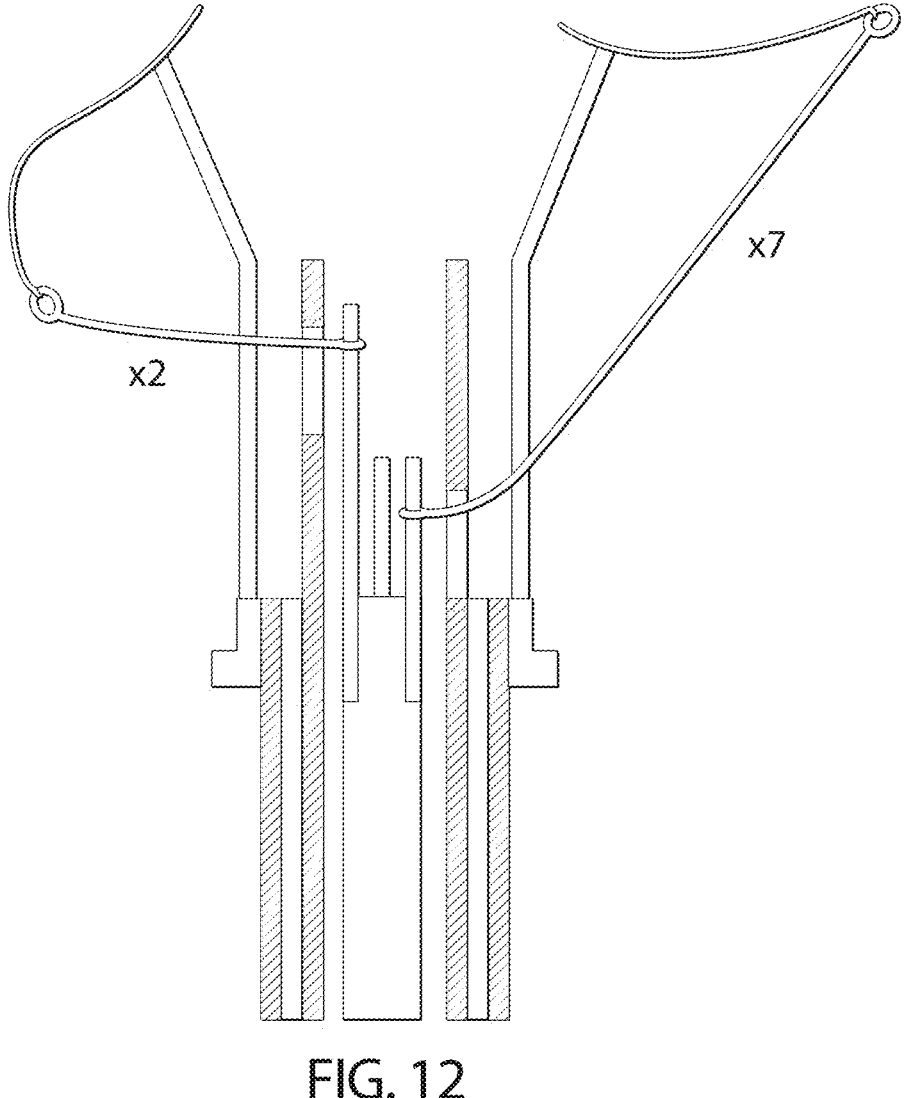
FIG. 12 is a cross-sectional view of the distal ends of the second and third shafts of the delivery system of FIG. 3, in accordance with an embodiment.

In some embodiments, the prosthetic heart valve may have a circumferentially asymmetric shape, which may require different means of attachment to the delivery system than what has previously been described herein. The embodiment of FIG. 13 includes nine thread-like elements, in which two of the thread-like elements are of equal size and shorter than the other seven thread-like elements which are themselves of equal size. In this embodiment, the thread-like elements may be included as a component of the delivery system or as a component of the prosthetic heart valve. The thread-like elements having different lengths are in this way configured to attach the delivery system to a prosthetic heart valve having anchoring members of different lengths. Also depicted in FIG. 12 is the capsule portion of the delivery system in which the second shaft includes one or more pins of different lengths, in which a distal end of a first pin extends farther distally than the distal ends of a second pin and a third pin. The one or more apertures of the third shaft of the embodiment in FIG. 12 also have different axial positions; a first aperture is located farther distally than a second aperture. Other embodiments may have different combinations of apertures, different locations of the apertures both circumferentially around the third shaft and axially along the length of the third shaft, different numbers of pins, different lengths of pins, and/or different axial locations of the distal ends of the one or more pins. In this way, the anchoring members of the prosthetic heart valve may be controlled regardless of the length or shape of each of the anchoring members.

Figure 13A:
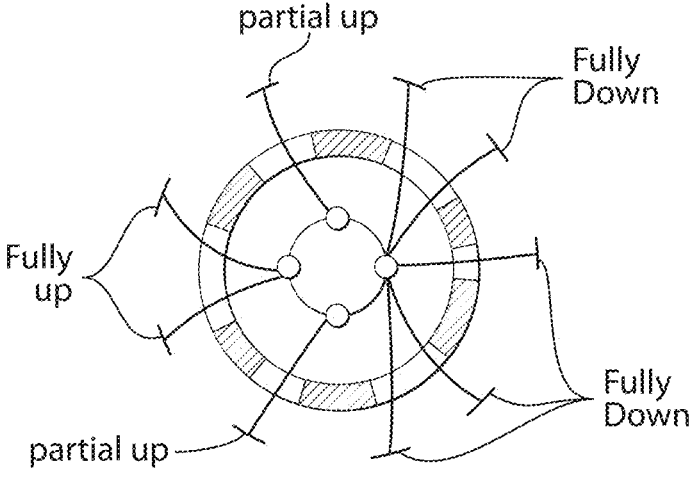
FIGS. 13A-13B are two views of the distal end of the second shaft of the delivery system of FIG. 3, in accordance with an embodiment.
Figure 13B:
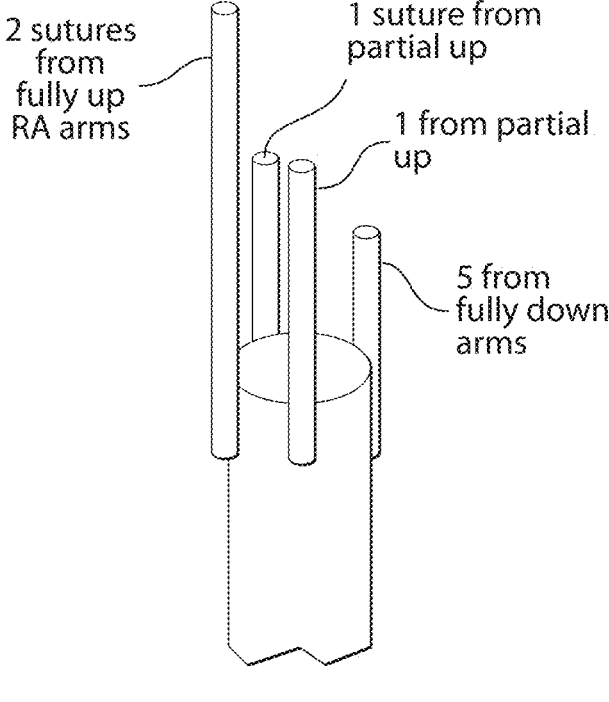

FIGS. 13A and 13B depict another embodiment in which the pins of the second shaft have different axial lengths. In this embodiment, four pins are included, which may be desirable for attaching to a prosthetic heart valve having anchoring members with three different lengths and/or shapes and/or circumferential locations.

Figure 14:
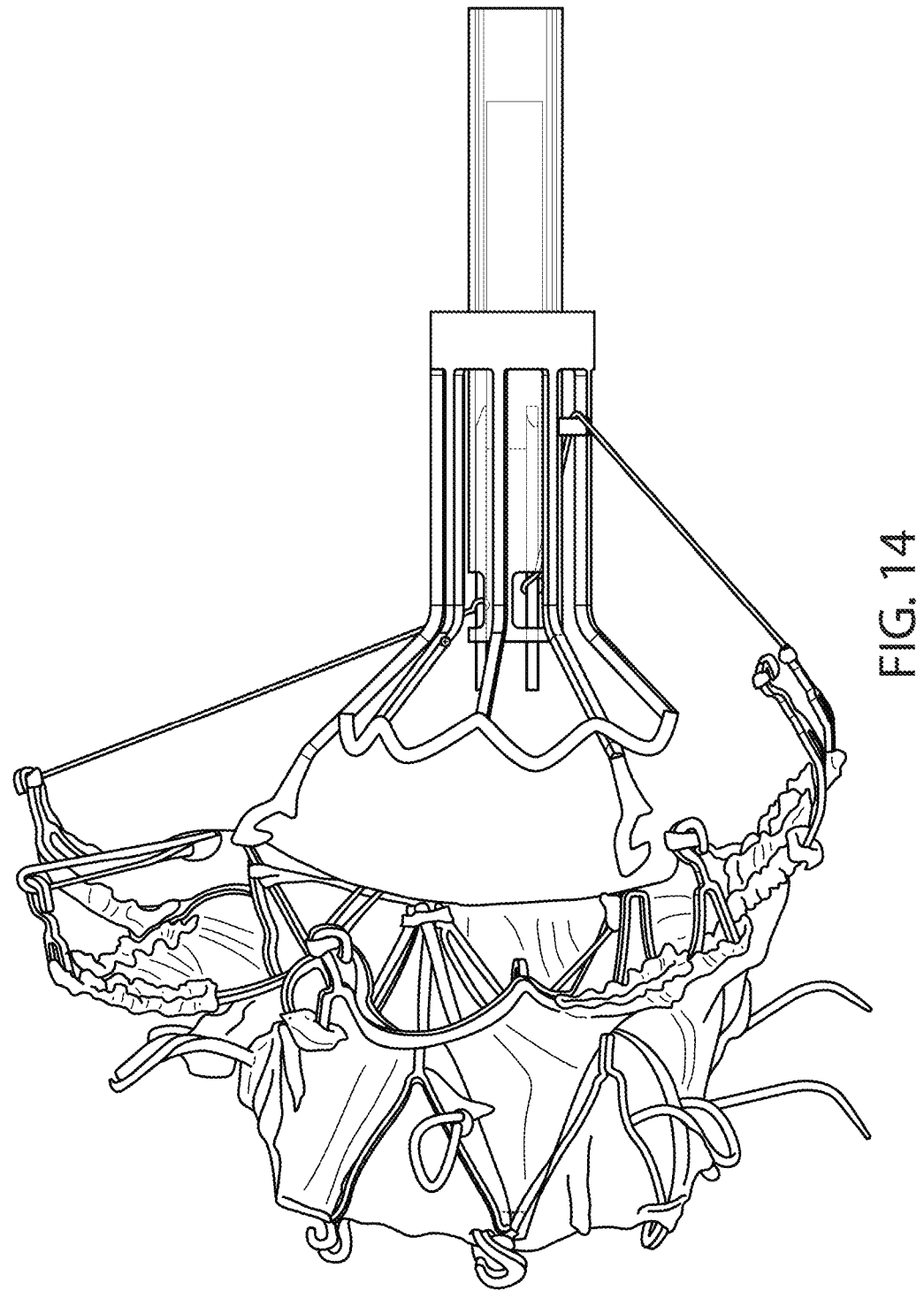
FIG. 14 is a side view of a prosthetic heart valve attached to a delivery system, in accordance with an embodiment.

FIG. 14 depicts another embodiment in which the prosthetic heart valve has anchoring members of different lengths. In this embodiment, an expandable frame of the delivery system includes at least one cross bar positioned between two axially-directed members of the expandable frame. This embodiment further includes one or more thread-like elements in which a first end of the one or more thread-like elements is attached to one or more pins of the second shaft of the delivery system, and an intermediate portion of the one or more thread-like elements is configured to contact a proximal side of the at least one cross bar when the attachment point of the one or more thread-like elements to the one or more pins moves farther distally than the at least one cross bar member. In this way, the delivery system may be configured to equilibrate the tension in the one or more thread-like elements when attached to anchoring members of the prosthetic heart valve having different lengths.

In some embodiments, a thread-like element has a first end with a first loop, a second end with a second loop, and an intermediate portion. The delivery system may be connected to a prosthetic heart valve by means of several thread-like elements, in which the first ends of the thread-like elements are connected to the prosthetic heart valve, and the second ends of the thread-like elements are connected to the pins of the second shaft of the delivery system. Also shown in this embodiment are at least one thread-like element in which the second end is disengaged from the delivery system.

The one or more thread-like elements (also referred to as tethers) may be made from any type of biocompatible thread, string, wire, cable, or line, for example using materials such as PTFE, polyester, silicone, PU, PE, PVC, PTFE, ETFE, FEP, PEBA, polyamide, a hydrogel material, nitinol, stainless steel, gold, platinum, titanium, other biocompatible metals, or a natural fiber such as silk. In some embodiments, the one or more thread-like elements may be made from a bioabsorbable material such as Polysorb or Vicryl. The one or more thread-like elements may be made from a continuous material, e.g., similar to a wire or rod, or may be braided from more than one individual lengths of material, e.g., similar to a cable, cord, rope, etc.

In some embodiments, the second shaft or the third shaft may include one or more longitudinal ribs, which are configured to allow the second shaft or the third shaft to bend along a plane that is perpendicular to a cross-sectional plane of the one or more longitudinal ribs, which may be advantageous to allow the second shaft or the third shaft to flex and thereby position a prosthetic heart valve inside a native heart.

Figure 15:
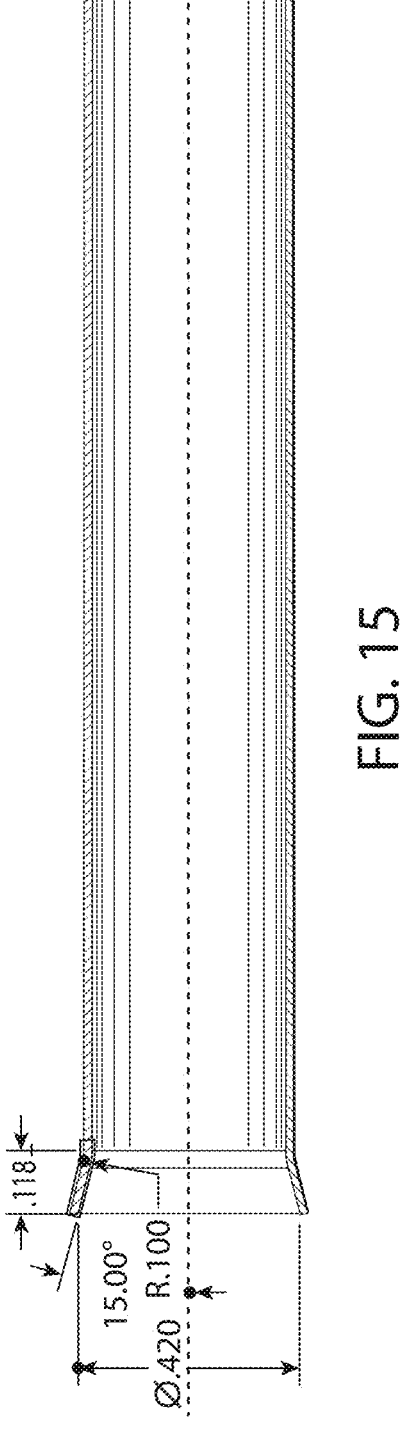
FIG. 15 is a cross-sectional side view of a capsule of a delivery system with a flared distal end, in accordance with an embodiment.
Figure 16:
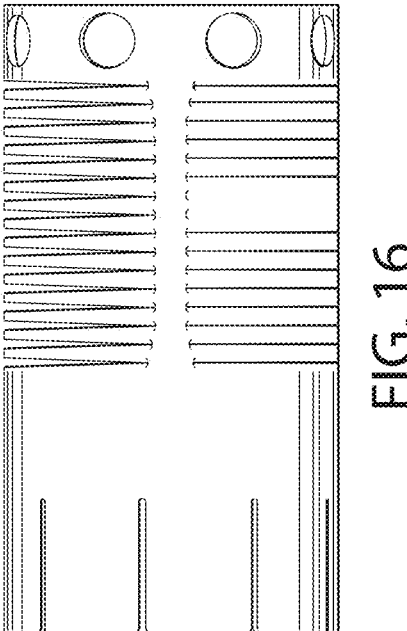
FIG. 16 is another top view of a capsule of a delivery system with a notched distal end, in accordance with an embodiment.

FIGS. 15-FIG. 18 depict several embodiments of the tube of the capsule portion of the delivery system disclosed herein. In some embodiments, a tube includes a distal portion, a first rib section comprising one or more longitudinal ribs proximal to the distal portion, a first ring portion proximal to the first rib section, a second rib section proximal to the first ring portion, a second ring portion proximal to the second rib section, a third rib section proximal to the second ring portion, and a proximal end. In some embodiments, the first ring portion, the second ring portion, and the proximal portion include at least one aperture configured to allow an inner liner of the tube and an outer liner of the tube (also not shown) to contact one another thereby helping secure the inner liner to the outer liner. The first rib section, second rib section, and third rib section each include one or more longitudinal ribs configured to allow the rib sections to bend along a plane that is perpendicular to a cross-sectional plane of the one or more longitudinal ribs and thereby position a prosthetic heart valve inside a native heart. In some embodiments, the tube includes one, two, or more than three rib sections. In some embodiments, the tube includes one or more than two ring portions. In some embodiments, the distal portion also includes one or more apertures. In some embodiments, any of the ring portions or the proximal portion is circumferentially uninterrupted, i.e., it includes no apertures. In some embodiments, an axial length of each of the rib sections is longer than an axial length of each of the ring portions or the distal end or the proximal end. However, in some embodiments, the axial length of one or more of the ring portions or the distal end or the proximal end may be greater than the axial length of one or more of the rib sections. In some embodiments, the apertures may be circular in shape, as shown in FIG. 16, although in other embodiments, the apertures may be of rectangular shape, elliptical shape, dogbone shape, etc.

The embodiment of FIG. 15 depicts a cross-sectional side view of a tube of a delivery system that includes a flared distal end, which may be desirable to facilitate entry of a prosthetic heart valve from an expanded configuration into a crimped configuration within an interior portion of the tube. The flared distal end may help to reduce forces on the delivery system when the prosthetic heart valve enters the tube of the capsule portion of the delivery system and enables the prosthetic heart valve to have a smaller maximum diameter when in a compressed configuration.

Figure 17:
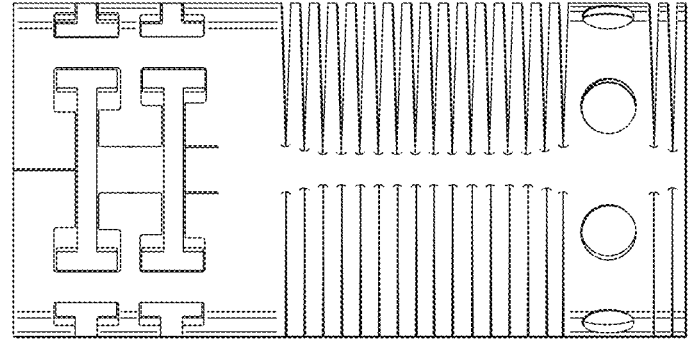
FIG. 17 is a side view of a capsule of a delivery system with slots and mating appendages located at a distal end, in accordance with an embodiment.
Figure 18:
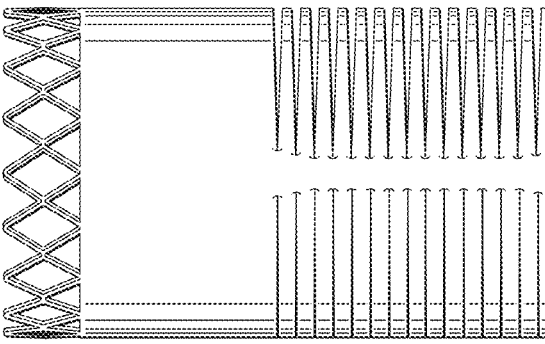
FIG. 18 is a side view of a capsule of a delivery system with an expandable support structure, in accordance with an embodiment.

FIG. 16-FIG. 18 depict several embodiments of a distal end of the tube of a delivery system which is configured to increase a diameter of the distal end relative to a diameter of the remaining portion of the tube, which may be desirable to facilitate entry of a prosthetic heart valve from an expanded configuration into a crimped configuration within an interior portion of the tube. In some embodiments, the distal end includes one or more tabs separated by one or more notches. FIG. 16 depicts an embodiment of the distal end of the tube of a delivery system in which the distal end includes nine tabs separated by nine notches. The embodiment of FIG. 16 may be advantageous for use with a prosthetic heart valve having an equal number of anchoring members (e.g., nine) that are configured to engage with the delivery system disclosed herein for transitioning from an expanded configuration into a crimped configuration within an interior portion of the tube. In some embodiments, a delivery system has an approximately sinusoidally-shaped distal end. In some embodiments, a delivery system includes a frame with a sinusoidally-shaped distal end.

FIG. 17 depicts an embodiment of the distal end of the tube of a delivery system in which the distal end includes one or more tabs separated by one or more notches, each tab comprising one or more circumferentially-directed appendages. In this embodiment, one or more of the appendages are generally T-shaped, with a distal end that has a width in an axial direction that is greater than a width in an axial direction of a proximal end of the one or more appendages. The one or more appendages may be configured to tesselate with one or more of the other appendages, as shown in FIG. 17. The embodiment of FIG. 17 may be configured to allow the one or more tabs of the distal end of the tube to expand in a radial direction to increase a diameter of the distal end relative to a diameter of the remaining portion of the tube, said radial expansion limited by the relative location of the one or more adjacent circumferentially-directed appendages. When the distal end of the tube expands, the underside of the circumferentially-directed appendages eventually contact one another, thereby preventing further expansion of the distal end of the tube. In different embodiments, the size and shape of the circumferentially-directed appendages size may be modified to allow for different maximum diameters of expansion of the distal end of the tube, depending on what is desired.

Figure 19:
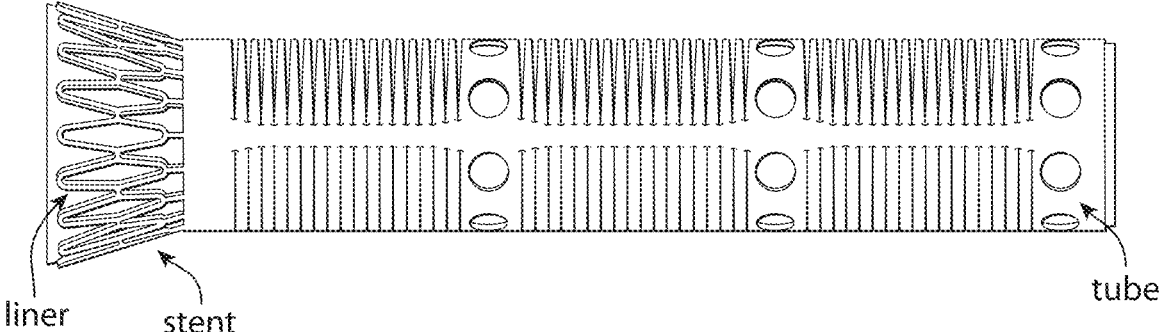
FIG. 19 is another side view of a capsule of a delivery system with an expandable support structure where the expandable support structure is in a flared position and a capsule has a lining material contacting an inner surface of a capsule, in accordance with an embodiment.

FIG. 18 depicts an embodiment of the distal end of the tube of a delivery system in which the distal end includes a stent. In some embodiments, the stent includes one or more distal apices and one or more proximal apices, in which the one or more proximal apices are attached to the tube of the delivery system. In some embodiments, the proximal apices are attached to the tube directly at the one or more proximal apices. In some embodiments, the proximal apices of the stent are attached to the tube through one or more axially-directed members. The tube may be configured to allow the stent to expand radially such that an axial distance between the one or more distal apices and the one or more proximal apices decreases and a diameter of the stent increases relative to a diameter of the tube. In some embodiments, the stent includes two or more sets of distal apices and one or more sets of proximal apices, in which the two or more sets of distal apices include at least a first set of distal apices and a second set of distal apices and the two or more sets of proximal apices include at least a first set of proximal apices and a second set of proximal apices, and in which the first set of distal apices is farther distal than the first set of proximal apices, the first set of proximal apices is farther distal than the second set of distal apices, and the second set of distal apices is farther distal than the second set of proximal apices, and so forth. The number of apices and sets of apices of the stent, as well as the height, width, thickness, and shape of the stent, may be adjusted to increase or decrease the diameter of the stent when radially expanded. FIG. 19 depicts a stent of the tube of a delivery system in which the stent is in an expanded configuration. FIG. 19 also depicts a liner that may be configured to cover an internal surface and/or an external surface of the tube of the delivery system, and may be configured to expand with the expansion of the stent into an expanded configuration.

In some embodiments, a delivery system comprises an approximately sinusoidally-shaped distal end and a proximal end comprising one or more axially-directed tabs. In some embodiments the tube of the delivery system may be configured to have two different structures at the distal end and proximal end, respectively, which may be advantageous by allowing either the distal end or the proximal end to be located in the distal-most position with respect to the delivery system, thereby reducing the number of tube components that must be kept available for testing different versions of tubes.

In some embodiments, a capsule of a delivery system comprises a notched distal end and an outer liner covering an external surface of the tube. In some embodiments, the tube may further include an inner liner which may be continuous with the outer liner. In some embodiments, the inner liner and outer liner may contact one another in between adjacent longitudinal ribs or through any of the apertures of the tube previously described. In some embodiments, the inner liner and/or the outer liner may be configured to increase a stiffness of the tube of the delivery system, or limit a maximum amount of flex of the tube. In some embodiments, the outer liner may be configured to increase lubricity of the tube which may be desirable to facilitate entry of the delivery system through a blood vessel of the body. In some embodiments, the inner liner and/or the outer liner may include one or more than one layers. In some embodiments, the inner liner and/or the outer liner may include one or more axially-directed strips. In some embodiments, the inner liner and/or the outer liner may include one or more radially-directed strips. In some embodiments, the inner liner and/or the outer liner may include one or more radially-wound strips.

In some embodiments, a prosthetic heart valve is in a crimped configuration within the tube of a delivery system, in which the tube includes a distal end comprising a stent and an outer liner.

In some embodiments, a tube of a delivery system comprises a distal end with circumferentially-directed appendages and an inner liner, and in which the rib sections bend along a plane that is perpendicular to a cross-sectional plane of the one or more longitudinal ribs.

Figure 20:
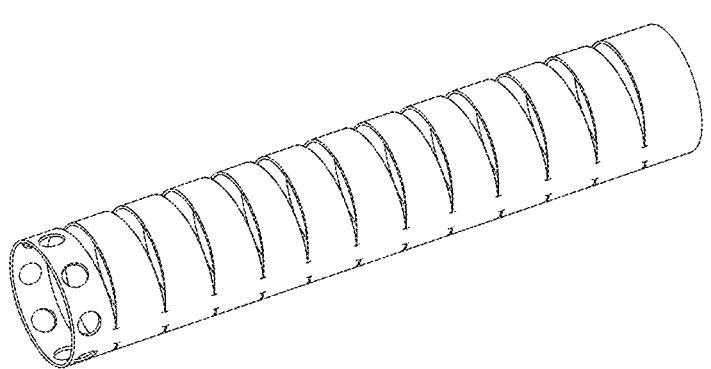
FIG. 20 is a perspective view of a capsule of a delivery system having slots that originate from a first side of an axial cross-sectional plane and that terminate on a second side of the axial cross-sectional plane, in accordance with an embodiment.

FIG. 20 depicts an embodiment of the tube of a delivery system in which the longitudinal ribs are configured to enable a greater degree of bend than the tube previously described. In some embodiments, one or more apertures may be located along an axially-directed spine of the tube. In the embodiment of FIG. 20, one or more apertures are located at a proximal end and/or a distal end of the tube. The one or more apertures may be configured to allow an outer liner and an inner liner to contact one another.

In some embodiments, the tube may be continuous with one of the shafts of the delivery system. For example, a distal end of the sixth shaft may comprise the tube such that the tube and the sixth shaft are continuous. In some embodiments, an outer diameter of the tube may be the same as an outer diameter of one of the shafts of the delivery system. In some embodiments, a liner may be disposed adjacent to an outer surface of the tube and one of the shafts of the delivery system such that the liner spans the proximal end of the tube and the distal end of the shaft of the delivery system. In some embodiments, the tube and sixth shaft of the delivery system are made from a single shaft with uniform outer diameter and uniform inner diameter, which may be desirable to reduce a loss in the angle of flex of the shafts of the delivery system during deployment of the prosthetic heart valve.

Figure 22:
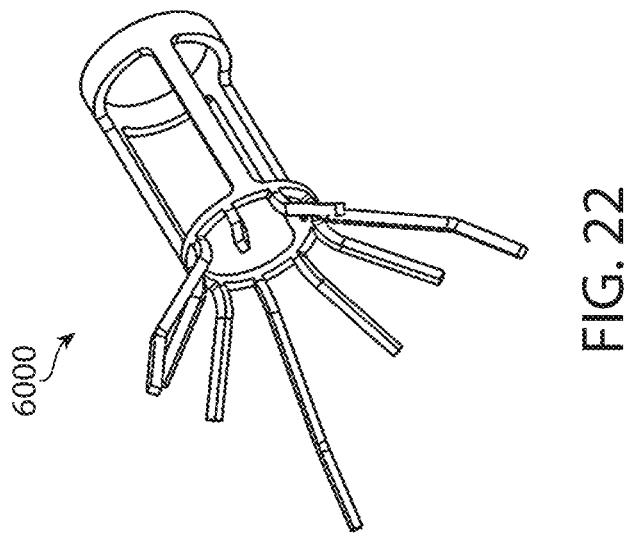
FIG. 22 is a perspective view of an expandable frame of the delivery system of FIG. 3 shown in an expanded configuration, in accordance with an embodiment.
Figure 21:
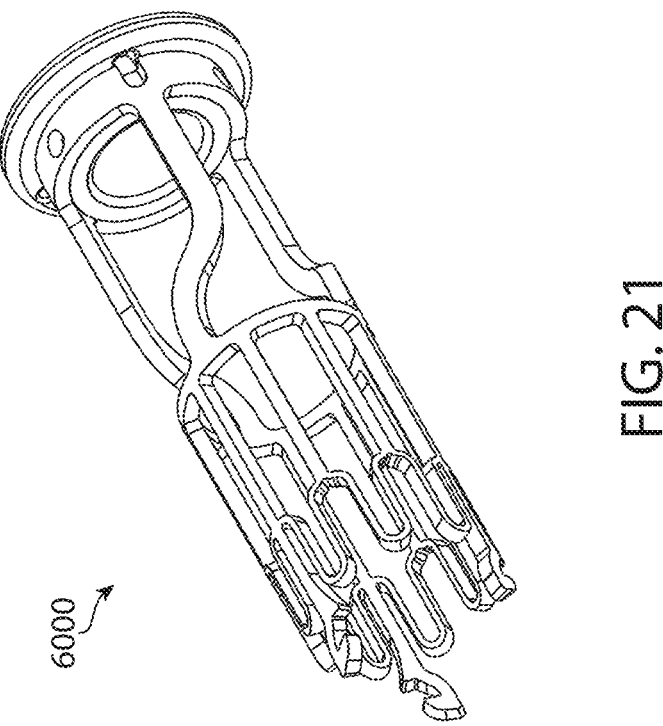
FIG. 21 is a perspective view of an expandable frame of the delivery system of FIG. 3 shown in a collapsed configuration, in accordance with an embodiment.
Figure 23:
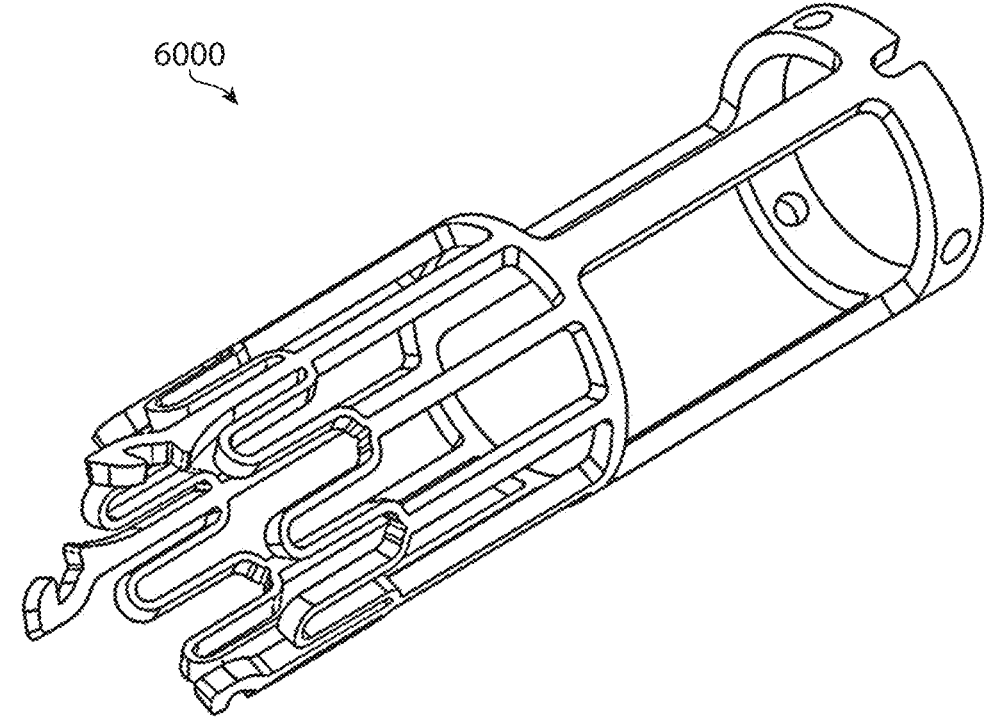
FIG. 23 is a perspective view of an expandable frame of the delivery system of FIG. 3 in a compressed configuration, in accordance with an embodiment.

FIG. 21-FIG. 23 depict several views and embodiments of an expandable frame 6000 of the delivery system disclosed herein. FIG. 21 depicts an embodiment in which the expandable frame 6000 is shown in a compressed configuration. The expandable frame includes a proximal ring, an expandable support structure, and a cylindrical portion disposed between the proximal ring and the expandable support structure. In some embodiments, the proximal ring includes one or more apertures, which may be spaced at intervals around the circumference of the proximal ring of the expandable frame. In the embodiment shown in FIG. 21, the proximal ring has six apertures, which may be desirable for facilitating attachment to one or more shafts of the delivery system, or for directing a cable, wire, cord, etc. to a more distal portion of the delivery system. The cylindrical portion of the expandable frame may include one or more axial members, which each may have a proximal end and a distal end. In some embodiments, the proximal end and the distal end of the one or more axial members may be axially aligned; however, in other embodiments, such as the one shown in FIG. 21, the distal end of the one or more axial members may be located circumferentially out of phase from the circumferential location of the proximal end of the one or more axial members, which may be desirable to help direct a cable, wire, cord, etc. to a more distal portion of the delivery system. In some embodiments, the axial members may be separated by a space sized to enable one or more anchoring members of the prosthetic heart valve to nest between adjacent axial members when the prosthetic heart valve is in a compressed configuration, thereby facilitating reentry of the prosthetic heart valve into the tube of the delivery system.

The expandable frame may include an expandable support structure configured to expand to a diameter that is greater than the diameter of the expandable frame in a compressed configuration, as displayed in FIG. 22. The expandable support structure may be configured to connect to a prosthetic heart valve. In some embodiments, the expandable support structure includes a plurality of arms spaced equally around the circumference of the expandable support structure. In some embodiments, the expandable support structure comprises at least 3, at least 4, at least 5, at least 6, at least 7, at least 8, at least 9, or at least 10 arms. In some embodiments, the support structure comprises 12 or less, 11 or less, 10 or less, 9 or less, 8 or less, 7 or less, 6 or less, 5 or less, or 4 or less arms. In an exemplary set of embodiments, the expandable support structure comprises nine arms. In an exemplary set of embodiments, three of the nine arms further include three distal hooks, which are configured to attach to three anchoring members of the prosthetic heart valve. In some embodiments, 1, 2, 3, 4, 5, 6, 7, 8, 9, 10, or all of the arms further include one or more distal hooks. In some embodiments, the arms of the expandable support structure includes one, two, or more than three hooks, such as six or nine hooks. In some embodiments, the expandable support structure is configured to provide stabilization to the prosthetic heart valve when the expandable frame is attached to the prosthetic heart valve (e.g., via a locking and release mechanism comprising three or more hooks). For example, without wishing to be bound by theory, having three points of contact between the expandable frame and the prosthetic heart valve may create a plane of contact to prevent rocking, rotation, and/or other undesired movement between the expandable frame and the prosthetic heart valve. In some embodiments, the expandable support structure includes one or more stent-like features that provide stabilization to the expandable frame, such as the sinusoidal or Z-shaped circumferential stent pattern depicted in FIG. 67. Such a stent-like feature may advantageously provide support between or among connection points of the expandable frame to the prosthetic heart valve that helps stabilize the prosthetic heart valve, in some cases. For example, the expandable support structure may provide this stabilization throughout deployment of the prosthetic heart valve, including in its crimped configuration and in its deployed configuration.

Advantageously, the locking/mating configurations described herein (e.g., comprising fasteners (e.g., hooks) on the expandable support structure) are configured to mate with any prosthetic heart valve. In some embodiments, the prosthetic heart valve comprises matching fasteners (e.g., hooks) which engage with the fasteners of the delivery system. In other embodiments, the prosthetic heart valve may have any number of configurations such that three or more points of contact engage with the fasteners of the delivery system. Advantageously, the delivery system described herein may be useful for the delivery, repositioning, and/or retrieval of various commercially available prosthetic heart valves and is not limited to the particular heart valve configurations described herein. Those of ordinary skill in the art would understand, based upon the teachings of this specification, how to select and deploy the delivery systems described herein such that they may engage with other prosthetic heart valves.

FIG. 23 depicts an embodiment of an expandable frame in a compressed configuration, in which the cylindrical portion includes three members whose distal ends and proximal ends are axially aligned. In some embodiments, an expandable frame in a compressed configuration does not include a cylindrical portion. In some embodiments, six arms of the expandable support structure comprise a distal end of each arm that includes a tab-like feature, which may be configured to connect to an anchoring member of the prosthetic heart valve.

Figures 24, 25, 26:
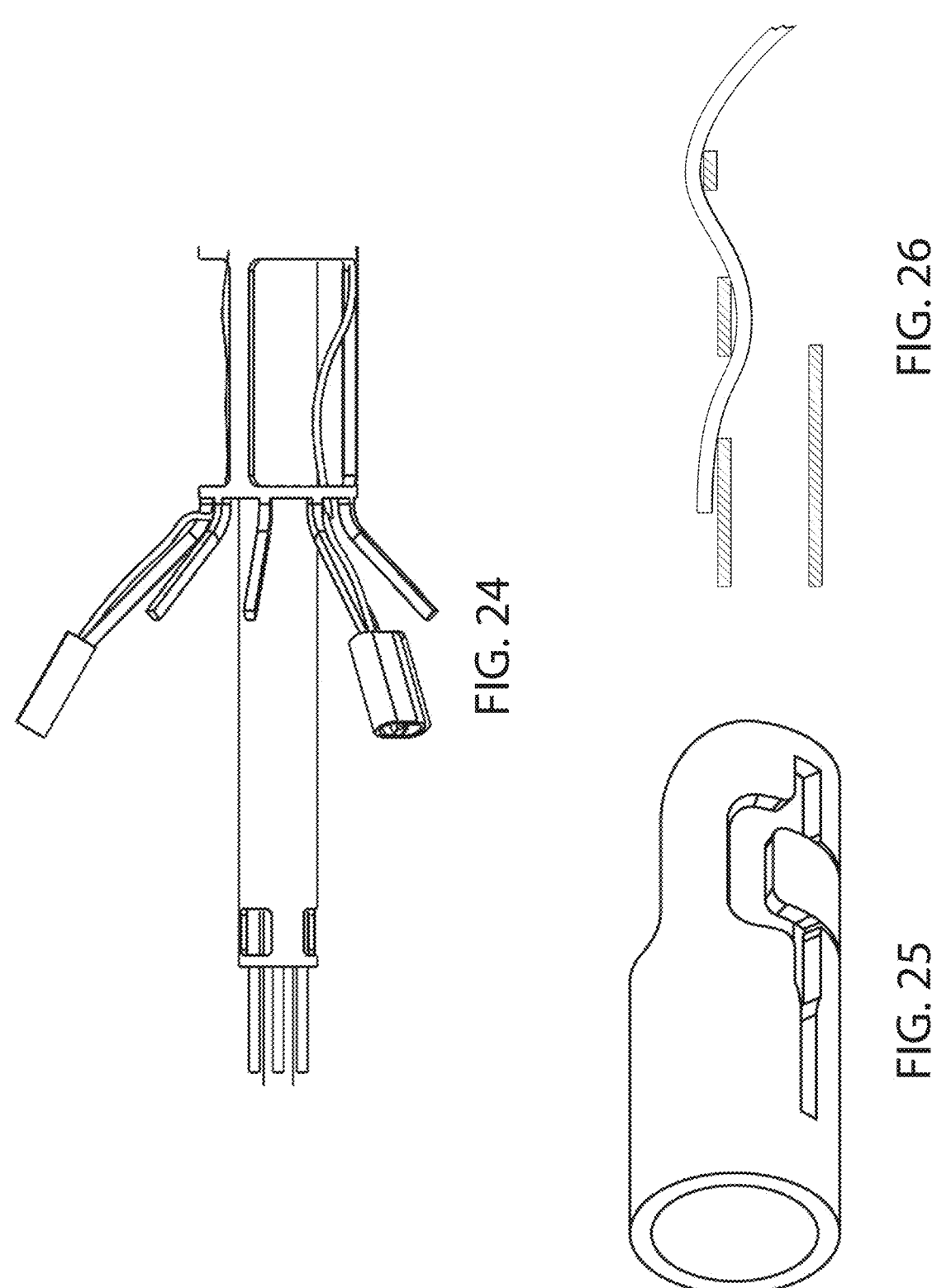
FIG. 24 is a side view of the expandable frame of the delivery system of FIG. 3 shown in an expanded configuration wherein at least one tube is configured to encompass at least one arm of the expandable frame, in accordance with an embodiment.
FIG. 25 is a perspective view of a sheath of the delivery system of FIG. 3, in accordance with an embodiment.
FIG. 26 is a side cross-sectional view of a sheath of the delivery system of FIG. 3, in accordance with an embodiment.

FIG. 24 is a side view of the capsule portion of the delivery system of FIG. 3, in which the expandable frame is shown in an expanded configuration and the delivery system includes at least one sheath configured to encompass at least one arm of the expandable frame. In the embodiment of FIG. 24, the delivery system includes three sheaths, each of which is configured to encompass a hook disposed at the distal end of three arms of the expandable support structure of the expandable frame. The sheaths may be configured to encompass at least one mating portion of the prosthetic heart valve when engaged with the hooks of the expandable support structure, thereby securely connecting the delivery system to the prosthetic heart valve.

In some embodiments, the sheaths may be attached to at least one pull wire 606, such as the one shown in FIG. 24, which may be configured to move axially in a proximal direction to disengage with the at least one mating portion of the prosthetic heart valve, thereby disconnecting the prosthetic heart valve from the delivery system. In some embodiments, the pull wires 606 may be routed through one or more apertures of the proximal ring of the expandable frame, which may be desirable to help protect the at least one pull wire 606 and/or allow a more direct route of travel.

In some embodiments, the sheath may form a cylinder with an approximately circular cross-sectional profile. In other embodiments, the sheath may have an elliptical or rectangular cross-sectional profile, such as the embodiment shown in FIG. 24. In the embodiment of FIG. 25, the sheath has a distal end with a circular cross-sectional profile, and a proximal end that includes a proximally-directed tab that forms less than the full circumference of the distal end. This may be advantageous to ensure the sheath may slide over the at least one arms of the expandable support structure. Also shown in FIG. 25 is a circumferentially-directed tab disposed within an intermediate portion of the sheath. The at least one pull wire 606 may be configured to enter a lumen of the sheath adjacent a proximal side of the circumferentially-directed tab, and exit the lumen of the sheath adjacent a distal side of the circumferentially-directed tab, as depicted in the side cross-sectional view of FIG. 26

Figure 27:
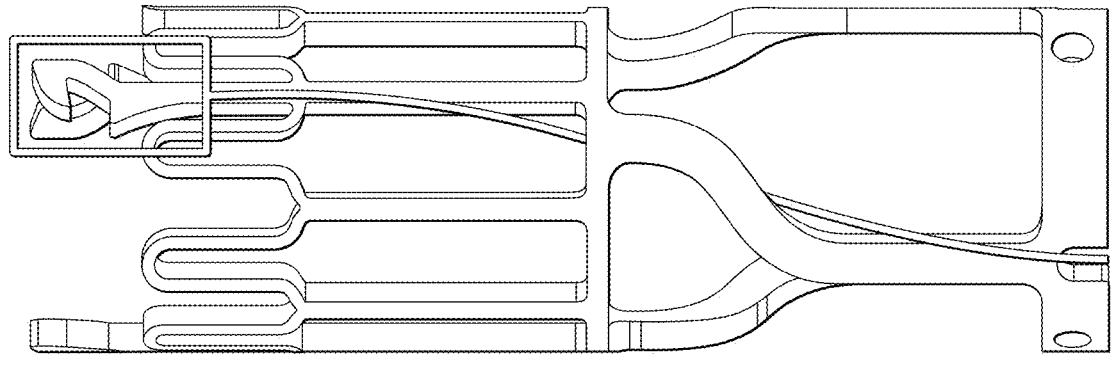
FIG. 27 is a side view of the expandable frame of the delivery system of FIG. 3 shown in a collapsed configuration wherein the at least one tube has an attachment member that traverses a proximal strut of the expandable frame on an internal side and traverses a distal strut of the expandable frame on an internal side, in accordance with an embodiment.

In the embodiment depicted in FIG. 27, the expandable frame of the delivery system of FIG. 3 is shown in a collapsed configuration in which the at least one pull wire 606 is attached to the at least one sheath and traverses a member of the cylindrical portion of the expandable frame. In FIG. 27, the at least one pull wire 606 traverses a member of the cylindrical portion of the expandable frame on an internal side and traverses an intermediate ring of the expandable frame on an internal side. In some embodiments, the at least one pull wire 606 traverses a member of the cylindrical portion of the expandable frame on an external side and traverses the intermediate ring of the expandable frame on an internal side. In some embodiments, the at least one pull wire 606 traverses the cylindrical portion of the expandable frame on an internal side and traverses the intermediate ring of the expandable frame on an external side. The embodiment of FIG. 27 may offer advantages for protecting the at least one pull wire 606 from damage in either a compressed or expanded state. The expandable frame disclosed herein is preferably made of Nitinol, but may also be made of other biocompatible materials, such as stainless steel. In some embodiments, the expandable frame may be directly attached to any one of the shafts of the delivery system. The expandable frame may further control expansion of the prosthetic heart valve. For example, in some embodiments the expandable frame may be attached to the fourth shaft of the delivery system (directly or indirectly) such that translation of the fourth shaft in a distal direction relative to the tube of the delivery system causes translation of the expandable frame, as well as the prosthetic heart to which the expandable frame is connected, out of the distal end of the tube of the delivery system, while also allowing the expandable frame and the prosthetic heart valve to expand. Hence, by controlling the translation of the fourth shaft of the delivery system relative to the tube of the delivery system, the expansion of both expandable frame and prosthetic heart valve may be controlled. Similarly, retraction of the expandable frame, for example by translating the fourth shaft of the delivery system proximally relative to the tube of the delivery system, may control collapsing of the expandable frame and the prosthetic heart valve and/or retraction into the tube of the delivery system.

Figure 28A:
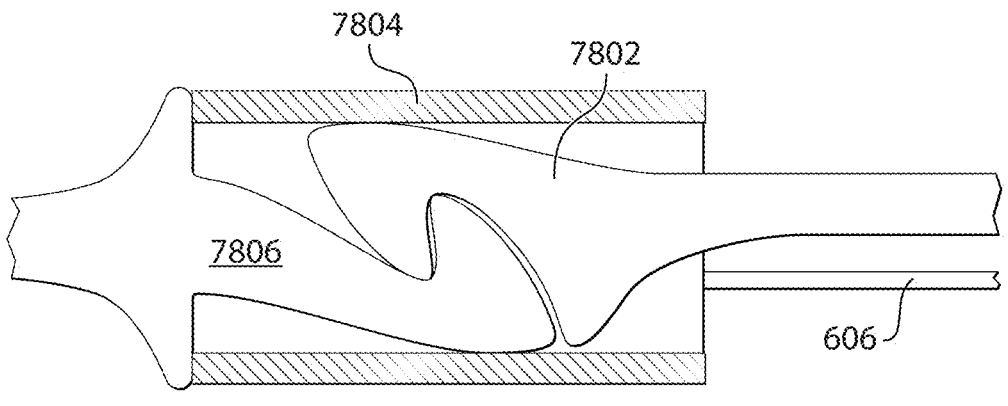
FIGS. 28A-28B are side cross-sectional views of embodiments of a fastener of the delivery system connected to a fastener of the prosthetic heart valve, in accordance with an embodiment.

FIG. 28 depicts an embodiment of a fastener 7802 (e.g., a hook) of the expandable frame 6000 in which a sheath 7804 with an attached pull wire 606 encompasses the hook. In this embodiment, the fastener 7802 is configured to nest securely with a mating fastener 7806 of the prosthetic heart valve, while the sheath 7804 is configured to prevent disengagement of the two fasteners 7802, 7806. In this way, the sheath 7804 provides a lock for ensuring connection of the delivery system to the prosthetic heart valve until the one or more pull wires 606 from the one or more sheaths are retracted to enable disengagement of the two hooks. In some embodiments, by ensuring the connection of the delivery system to the prosthetic heart valve, the prosthetic heart valve may be positioned within the native heart valve in an implanted position while maintaining a coupling with the delivery system. In some cases, the prosthetic heart valve may need to be recaptured, for example, because of incorrect placement in the native heart valve, a perceived risk to the native heart, or other reason. The coupling to the delivery system during implantation may enable the delivery system to recapture the prosthetic heart valve. In some embodiments, the prosthetic heart valve may be repositioned within the capsule portion of the delivery system. The recaptured prosthetic heart valve may be repositioned in the native heart valve or removed from the body. In some embodiments, the prosthetic heart valve may be deployed, repositioned (e.g., recapturing and positioning), and deployed again any suitable number of time. For example, the delivery system may be used to reposition the placement of the prosthetic heart valve one, two, three, four, five, or more times (e.g., until the prosthetic heart valve is positioned in the desired location and/or configuration). In an exemplary set of embodiments, the delivery system deploys the prosthetic heart valve such that the prosthetic heart valve attaches to the native leaflets of the native heart valve and, in the case that the prosthetic heart valve does not reliably attach to the native leaflets, the prosthetic heart valve may be recaptured and/or repositioned until the prosthetic heart valve attaches to the native leaflets of the native heart valve.

In various embodiments, the fastener may be any type of mating element, e.g., a hook, a clasp, a clip, a catch, a pin, a hook-and-eye, a buckle, a latch, a lock, a snap, a button, a slide, etc.

The pull wire 606 may be attached to the sheath, for example, by welding, crimping, or adhesive bonding. The sheath may be made of any biocompatible material, but preferably from a metal such as Nitinol, stainless steel, titanium, gold, etc. The pull wire may be made from any biocompatible material including Nitinol, stainless steel, titanium, gold, PTFE, polyester, silicone, PU, PE, PVC, PTFE, ETFE, FEP, PEBA, polyamide, a hydrogel material, or a natural fiber (e.g., silk). The pull wire may be made from a continuous material, e.g., similar to a wire or rod, or may be braided from more than one individual lengths of material, e.g., similar to a cable, cord, rope, etc. In other embodiments, the pull wire 606 may be made from one or more interconnected loops of material. In some embodiments, the pull wire 606 may be made of one or more bodies, connected by one or more lengths of material.

In some embodiments, the delivery system includes an adapter that is configured to attach the expandable frame to the fourth shaft of the delivery system. The adapter may be advantageous if, for example, the expandable frame is made from a different material than the fourth shaft. For example, the expandable frame may be made from Nitinol and the fourth shaft may be made from stainless steel, which may be difficult to join through conventional means and the adapter may be configured to facilitate connection between the two components. In some embodiments, an adapter includes a proximal ring, a distal ring, and a central lumen that passes through both the proximal ring and distal ring. A diameter of the proximal ring is greater than a diameter of the distal ring. One or more axially-directed apertures may be located on the proximal ring, which may be desirable to allow passage therethrough of one or more pull wires 606. The distal ring may include one or more radially-directed apertures, which may be used to facilitate attachment to the expandable frame, for example by welding, or insertion of another component such as a screw, bolt, rivet, etc. In some embodiments, the adapter includes three axially-directed apertures and three radially-directed apertures. The diameter of the central lumen of the adapter may be configured to fit snugly around the outer perimeter of a distal end of the fourth shaft. The outer diameter of the distal ring of the adapter may be configured to fit snugly within the inner perimeter of the proximal ring of the expandable frame. The adapter may be made of numerous different biocompatible materials but is preferably made from the same material as either the expandable frame or the fourth shaft and is preferably made from either Nitinol or stainless steel.

In some embodiments, the expandable frame may be attached to a distal end of the fourth shaft of the delivery system and the first shaft, second shaft, third shaft, fifth shaft, sixth shaft, and the tube of the capsule portion may be configured to move in an axial direction either proximally or distally relative to the fourth shaft of the delivery system. In such a way, the axial depth of the prosthetic heart valve may be increased or decreased while maintaining the first bend of the six shafts of the delivery system and the second bend of the six shafts of the delivery system, thereby enabling greater control over the placement of the prosthetic heart valve within the native heart.

In some embodiments, the sixth shaft of the delivery system may include an outer liner that is configured to have different flexibility at different portions along the length of the shaft. For example, the outer liner could be made from more than one material, more than one material durometer, and/or more than one thickness, which may be advantageous to achieve a desired level of flexibility of the delivery system shafts in one or more planes of steering. In some embodiments, a delivery system in which a distal portion of the shaft is made from a first material and a proximal portion of the shaft is made from a second material, which enables the bend region of the shaft to be located over a shorter distance with a smaller radius in the distal portion of the shaft than might otherwise be the case.

Figures 28B, 29A, 29B, 29C:
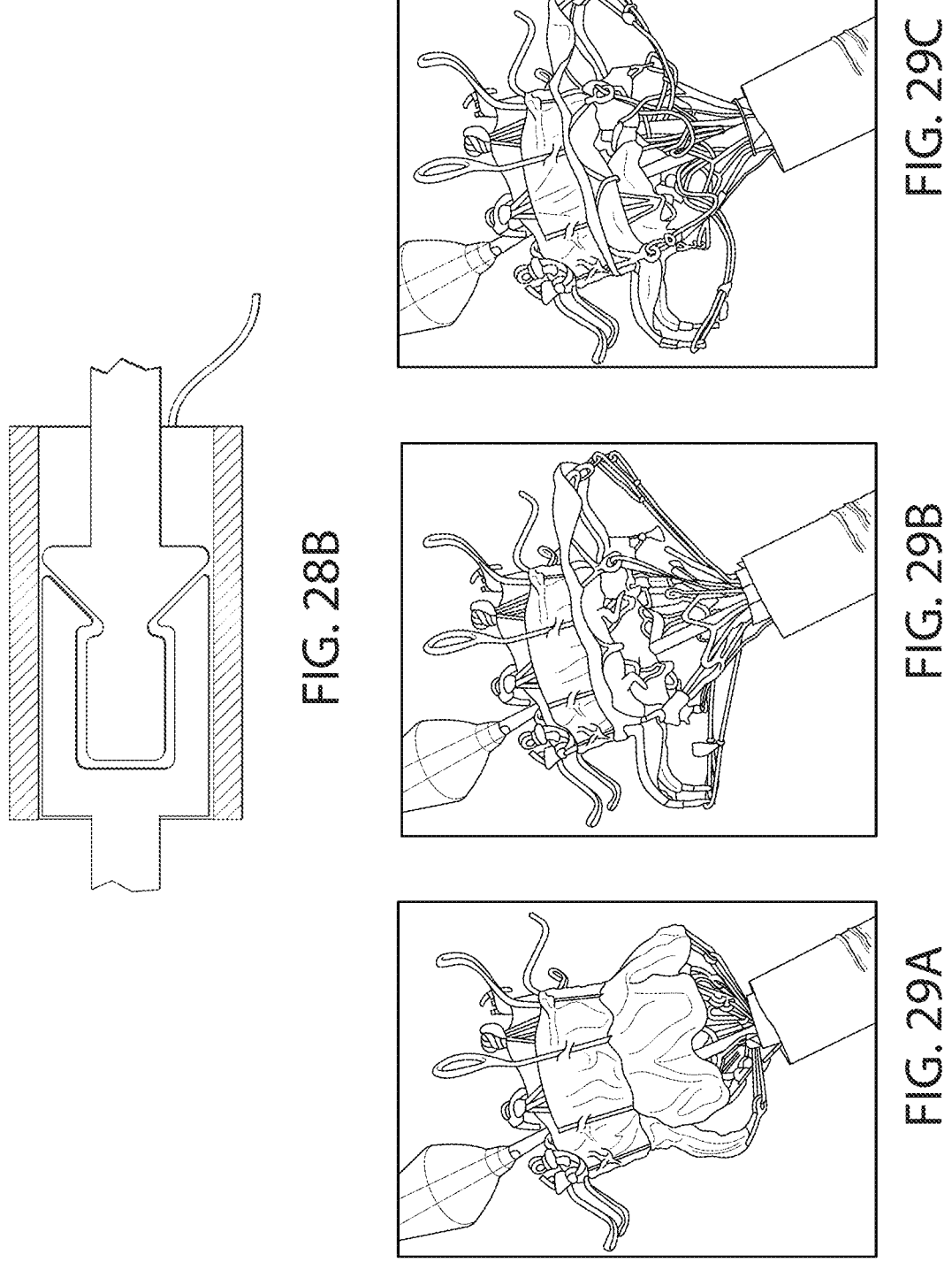
FIGS. 29A-29C depicts a prosthetic heart valve attached to a delivery system moving from an expanded configuration to a deployed configuration, in accordance with an embodiment.
Figures 30A, 30B, 30C:
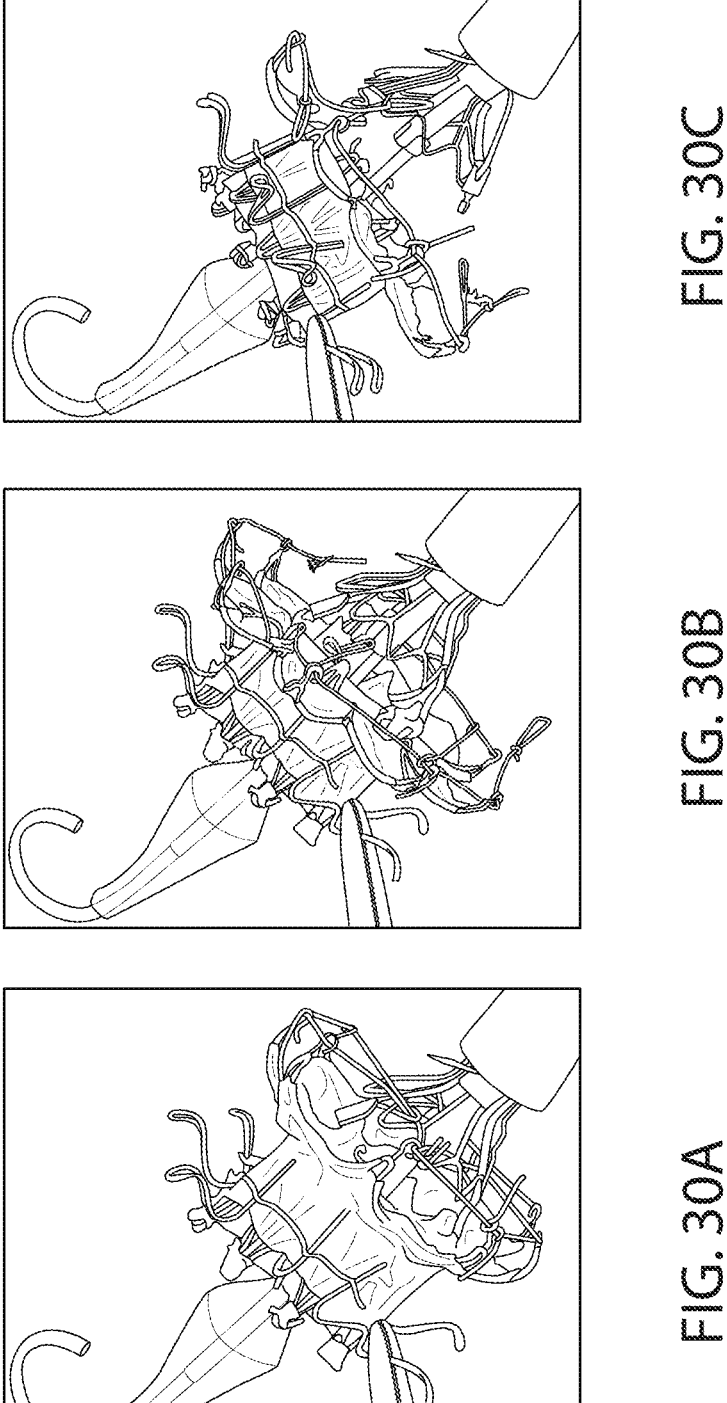
FIGS. 30A-30C depicts a prosthetic heart valve attached to a delivery system moving from a deployed configuration to an implanted configuration, in accordance with an embodiment.

FIG. 29A-FIG. 30C depict various stages of deployment of an embodiment of an exemplary prosthetic heart valve which is at least initially attached to a delivery system. In FIG. 29A, the prosthetic heart valve is shown attached to the expandable frame of the delivery system while several of the arms of the prosthetic heart valve are connected to the delivery system by several thread-like elements. As described previously, advancing the expandable frame (and therefore the prosthetic heart valve as well) relative to the tube of the delivery system may cause the expandable frame and the prosthetic heart valve to advance out of the distal end of the tube of the delivery system and expand in the space beyond the distal end of the tube of the delivery system. As depicted in FIG. 29B, the shafts of the delivery system securing the thread-like elements may be advanced relative to the other shafts of the delivery system to articulate the arms of the prosthetic heart valve (for example, to lower the arms of the prosthetic heart valve into a deployed configuration). Similarly, the shafts of the delivery system securing the thread-like elements may be retracted relative to the other shafts of the delivery system to articulate the arms of the prosthetic heart valve (for example, to raise the arms of the prosthetic heart valve into a collapsed or crimped configuration). In such a way, the prosthetic heart valve may be deployed into the native tricuspid valve, whereupon the prosthetic heart valve may be fully anchored or fixed at, near, or within the native tricuspid valve, while still retaining the ability to re-articulate the arms of the prosthetic heart valve to allow repositioning of the prosthetic heart valve and subsequent re-deployment of the prosthetic heart valve. This capability allows an assessment of the hemodynamic function of the prosthetic heart valve, prior to disengaging the prosthetic heart valve into an implanted configuration in the native heart. FIG. 29C depicts a subsequent step of releasing the thread-like elements to disengage from the arms of the prosthetic heart valve. The expandable frame may also be disengaged from the prosthetic heart valve, either before or after releasing the thread-like elements, an illustration of which may be seen in FIG. 30C.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" may refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article may only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article may only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

It is understood that some or all steps, operations, or processes may be performed automatically, without the intervention of a user. Method claims may be provided to present elements of the various steps, operations or processes in a sample order, and are not meant to be limited to the specific order or hierarchy presented.

The Title, Background, Brief Description of the Drawings, and Claims of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it may be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims s reflect, inventive subject matter lies in less than all features of a single disclosed configuration or operation. The following claims are hereby incorporated into the Detailed Description, with each claims standing on its own to represent separately claimed subject matter.

What is claimed is:

1. A delivery system for delivering a prosthetic heart valve to a native heart valve of a heart, the system comprising:
   a shaft portion;
   a handle portion coupled to a proximal end of the shaft portion;
   a capsule portion coupled to a distal end of the shaft portion and configured to house the prosthetic heart valve; and
   at least one shaft, at least one steering wire, and at least one pull wire,
   wherein the at least one shaft, at least one steering wire, and/or the at least one pull wire is configured to extend from the handle portion through the shaft portion to the capsule portion of the delivery system,
   wherein the capsule portion comprises a tubular portion that comprises an expandable frame comprising a plurality of frame members,
   wherein the plurality of frame members comprises an expandable support structure, and wherein the expandable support structure is configured to attach to one or more portions of the prosthetic heart valve,
   wherein the native heart valve comprises a plurality of native leaflets, and wherein the delivery system is configured to deploy the prosthetic heart valve such that the prosthetic heart valve grasps the plurality of native leaflets without directly attaching to a native annulus and/or without directly attaching to a native chord of the native heart valve such that the prosthetic heart valve may be retrieved and/or repositioned within the native heart valve by the delivery system, and
   wherein, upon deployment, the prosthetic heart valve is axially stabilized within the native heart valve by grasping the plurality of native leaflets of the native heart valve,
   wherein, after deployment, at least one portion of the delivery system is capable of re-engaging the prosthetic heart valve to reposition the prosthetic heart valve within the native heart valve and/or retrieve the prosthetic heart valve into the capsule portion of the delivery system.

2. The delivery system of claim 1, wherein:
   the plurality of frame members further comprises one or more fasteners configured to attach to a corresponding fastener on the prosthetic heart valve.

3. The delivery system of claim 2, further comprising one or more tubes configured to maintain contact between one or more fasteners of the delivery system and the prosthetic heart valve.

4. The delivery system of claim 3, wherein the at least one pull wire is attached to the one or more tubes.

5. The delivery system of claim 1, wherein an inner shaft extends through the shaft portion, and a distal portion of the inner shaft is disposed in a lumen of the tubular portion.

6. The delivery system of claim 5, wherein the tubular portion comprises a tapered head member coupled to the distal portion of the inner shaft.

7. The delivery system of claim 6, wherein at least a portion of the tapered head member is disposed in the tubular portion.

8. The delivery system of claim 5, wherein the shaft portion further comprises a plurality of nested shafts, and the plurality of nested shafts comprise the inner shaft.

9. The delivery system of claim 8, wherein at least one shaft of the plurality of nested shafts further comprises an outer shaft.

10. The delivery system of claim 1, wherein the tubular portion is configured to adjust a position of the prosthetic heart valve relative to the handle portion.

11. The delivery system of claim 1, wherein the at least one steering wire is configured to flex the shaft portion to an angle up to approximately 125 degrees from a longitudinal axis of the handle portion.

12. The delivery system of claim 1, wherein the at least one steering wire is configured to flex the shaft portion to an angle up to approximately 30 degrees from a longitudinal axis of the handle portion.

13. The delivery system of claim 1, wherein:
the at least one steering wire comprises a first steering wire and a second steering wire,
the first steering wire is configured to flex the shaft portion in a first plane from a longitudinal axis of the handle portion, and
the second steering wire is configured to flex the shaft in a second plane from the longitudinal axis.

14. The delivery system of claim 1, wherein a proximal end of the at least one pull wire is disposed within the handle portion, and
a distal end of the at least one pull wire is disposed within the capsule portion.

15. The delivery system of claim 1, wherein the at least one pull wire is configured to control release of the prosthetic heart valve from the delivery system.

16. The delivery system of claim 1, further comprising at least one tether for coupling the shaft portion to the prosthetic heart valve.

17. The delivery system of claim 16, wherein the at least one shaft comprises:
an inner shaft disposed within a lumen of an outer shaft, wherein:
the inner shaft comprises at least one pin to which at least one thread is coupled,
the outer shaft comprises at least one aperture through which the at least one thread is disposed, and
a displacement of the inner shaft within the outer shaft decouples the at least one thread from the at least one pin.

18. The delivery system of claim 1, wherein the capsule portion comprises a flexible tube configured to flex within at least one plane.

19. The delivery system of claim 18, wherein:
the flexible tube comprises a metal tube defining a first plurality of apertures along a first side and a second plurality of apertures along a second side, and
the first side is opposite the second side.

20. The delivery system of claim 1, wherein the at least one portion of the delivery system is configured to access a native blood vessel to deliver the prosthetic heart valve to the heart.

21. The delivery system as in claim 1, wherein the delivery system is configured to biodynamically fix the prosthetic heart valve to the native leaflets of the native heart valve.

22. A delivery system, comprising:
a shaft portion comprising at least one shaft, at least one steering wire, and at least one pull wire;
a handle portion coupled to a proximal end of the shaft portion; and
a capsule portion coupled to a distal end of the shaft portion and configured to house an implant,
wherein at least one portion of the delivery system is configured to be engaged with the implant while the implant is deployed within a subject such that the implant may be repositioned after deployment,
wherein the delivery system comprises one or more pins, one or more apertures, and one or more thread-like elements,
wherein the delivery system is configured to deploy the implant such that the implant grasps a plurality of native leaflets of a native heart valve without directly attaching the implant to a native annulus and/or native chords of the native heart valve,
wherein the implant is configured to move within the native heart valve in response to alternating pressure differentials on either side of the native heart valve during cardiac cycles of the heart, and
wherein, upon deployment, the implant is axially stabilized within the native heart valve by grasping the plurality of native leaflets of the native heart valve.

23. A method for delivering a prosthetic heart valve to a native heart valve of a heart, the method comprising:
advancing, by a delivery system comprising a capsule portion housing the prosthetic heart valve, the prosthetic heart valve through a native blood vessel and in proximity to the native heart valve; and
implanting the prosthetic heart valve in the native heart valve,
wherein the native heart valve comprises a plurality of leaflets,
wherein the delivery system deploys the prosthetic heart valve such that the prosthetic heart valve grasps the plurality of leaflets of the native heart valve without directly attaching the prosthetic heart valve to a native annulus and/or without directly attaching to a native chord of the native heart valve,
wherein the prosthetic heart valve is axially stabilized within the native heart valve by grasping the plurality of leaflets of the native heart valve,
wherein the prosthetic heart valve moves within the native heart valve in response to alternating pressure differentials on either side of the native heart valve during cardiac cycles of the heart, and
wherein, after deployment, the delivery system is capable of repositioning the prosthetic heart valve within the native heart valve and/or retrieving the prosthetic heart valve into the capsule portion of the delivery system.

* * * * *